US011925672B2

(12) United States Patent
Lee et al.

(10) Patent No.: US 11,925,672 B2
(45) Date of Patent: Mar. 12, 2024

(54) PEPTIDE HAVING ANTIOXIDANT ACTIVITY AND COMPOSITION CONTAINING SAME

(71) Applicant: SEMPIO FOODS COMPANY, Seoul (KR)

(72) Inventors: Dae Hee Lee, Daegu (KR); Haet Nim Um, Chungcheongbuk-do (KR); Moon Kyung Jeong, Sejong-si (KR); Mi Na Hong, Chungcheongbuk-do (KR); Jung Hee Park, Gyeonggi-do (KR); Yong Hahk Park, Seoul (KR); Byung Serk Hurh, Sejong-si (KR)

(73) Assignee: SEMPIO FOODS COMPANY, Seoul (KR)

( * ) Notice: Subject to any disclaimer, the term of this patent is extended or adjusted under 35 U.S.C. 154(b) by 363 days.

(21) Appl. No.: 17/266,811

(22) PCT Filed: Aug. 8, 2019

(86) PCT No.: PCT/KR2019/009972
§ 371 (c)(1),
(2) Date: Feb. 8, 2021

(87) PCT Pub. No.: WO2020/032622
PCT Pub. Date: Feb. 13, 2020

(65) Prior Publication Data
US 2022/0175871 A1 Jun. 9, 2022

(30) Foreign Application Priority Data
Aug. 8, 2018 (KR) .................. 10-2018-0092237

(51) Int. Cl.
A61K 38/06 (2006.01)
A61K 38/05 (2006.01)
A61P 39/06 (2006.01)

(52) U.S. Cl.
CPC .............. *A61K 38/06* (2013.01); *A61K 38/05* (2013.01); *A61P 39/06* (2018.01)

(58) Field of Classification Search
CPC .......... A61K 38/06; A61K 38/05; A61P 39/06
See application file for complete search history.

(56) References Cited

U.S. PATENT DOCUMENTS

| 8,106,020 | B2 | 1/2012 | Ohsu |
| 9,034,403 | B2 | 5/2015 | Nishiuchi |
| 9,420,813 | B2 | 8/2016 | Nagasaki et al. |
| 2005/0196836 | A1 | 9/2005 | Nishiuchi et al. |
| 2014/0120233 | A1* | 5/2014 | Kato .............. A23L 27/88 426/534 |
| 2016/0367621 | A1 | 12/2016 | Demopoulos et al. |

FOREIGN PATENT DOCUMENTS

| KR | 10-2016-0116600 | 10/2016 |
| WO | 2014017485 | 1/2014 |

OTHER PUBLICATIONS

Leslie et al, Structural Requirements for Functional Interaction of Glutathione Tripeptide Analogs with the Human Multidrug Resistance Protein 1 (MRP1), The Journal of Pharmacology and Experimental Therapeutics, 2003, 304, pp. 643-653.*
Calcagni et al, Novel glutathione analogues containing the dithiol and disulfide form of the Cys-Cys dyad, Amino Acids, 1999, 17, pp. 257-265.*
Drumm et al, Genetic Variation and Clinical Heterogeneity in Cystic Fibrosis, Annu. Rev. Pathol. Mech. Dis., Jul. 2012, pp. 267-282.*
Yampolsky et al, The Exchangeability of Amino Acids in Proteins, Genetics, 2005, 170, pp. 1459-1472.*
Mekky et al, Profiling of phenolic and other compounds from Egyptian cultivars of chickpea (*Cicer arietinum* L.) and antioxidant activity: a comparative study, RSC Adv., May 2015, pp. 17751-17767.*
Worden, Antioxidants and oxidative stress, from Netdoctor, 2016, pp. 1-7.*
Pubchem, Compound Summary, Norophthalmic acid, CID: 5489007, Aug. 8, 2005.
Amino, Y., et al., "Structure-CaSR-Activity Relation of Kokumi γ-Glutamyl Peptides," Chem. Pharm. Bull. 64, 1181-1189 (2016).
Mirzaei, M., et al., "Purification and identification of antioxidant and ACE-inhibitory peptide from *Saccharomyces cerevisiae* protein hydrolysate," Journal of Functional Foods 19 ( 2015) 259-268.
Alam, N., et al., "Review on in vivo and in vitro methods evaluation of antioxidant activity," Saudi Pharmaceutical Journal (2013) 21, 143-152.
Schapira, A.H.V., "Oxidative stress and mitochondrial dysfunction in neurodegeneration," Current Opinion in Neurology, Sep. 1996:260-264.
Mates, J.M., et al., "Antioxidant Enzymes and Human Diseases," Clinical Biochemistry, vol. 32, No. 8, 595-603, 1999.
Vranković, J., et al., "Antioxidant enzymes and GST activity in natural populations of Holandriana holandrii from the Bosna River," Turk J Biol, 36 (2012) 477-485.

(Continued)

*Primary Examiner* — Li N Komatsu
(74) *Attorney, Agent, or Firm* — DUANE MORRIS LLP; Gregory M. Lefkowitz; Brandon A. Chan

(57) ABSTRACT

The present invention provides a functional peptide having excellent antioxidant activity, the peptide having excellent biocompatibility and significantly better antioxidant activity than conventional GSHs in order to overcome the limitation of the weak antioxidant activity of existing peptides. The peptide of the present invention can promote antioxidant activity or effectively repair biological tissue or cell damage caused by reactive oxygen species generated due to oxidative stress. Therefore, the peptide having such antioxidant activity effectively acts on cell damage caused by oxidative stress, and can thus be used to prevent and repair cell damage.

7 Claims, 10 Drawing Sheets

Specification includes a Sequence Listing.

(56) References Cited

OTHER PUBLICATIONS

Lee, J.M., et al., "An Important Role of Nrf2-ARE Pathway in the Cellular Defense Mechanism," Journal of Biochemistry and Molecular Biology, vol. 37, No. 2, Mar. 2004, pp. 139-143.
Baird, L., et al., "The cytoprotective role of the Keap1-Nrf2 pathway," Arch Toxicol (2011) 85:241-272.
Gavin Ferguson, Wallace Bridge. "Glutamate cysteine ligase and the age-related decline in cellular glutathione: The therapeutic potential of γ-glutamylcysteine," Archives of Biochemistry and Biophysics, vol. 593, pp. 12-23 (Feb. 2, 2016) ISSN 0003-9861.

* cited by examiner

PEPTIDE HAVING ANTIOXIDANT ACTIVITY AND COMPOSITION CONTAINING SAME

CROSS-REFERENCE TO RELATED APPLICATIONS

This application is a § 371 national stage entry of International Application No. PCT/KR2019/009972, filed on Aug. 8, 2019, which claims priority to Korean Patent Application No. 10-2018-0092237, filed on Aug. 8, 2018, the entire contents of which are incorporated herein by reference.

SEQUENCE LISTING

The instant application contains a Sequence Listing, which has been submitted electronically in ASCII format, and is hereby incorporated by reference in its entirety. Said ASCII text file, created on Oct. 16, 2023, is named PCT628US_ST25 and is 28,672 bytes in size.

TECHNICAL FIELD

The present invention relates to a biocompatible peptide material having antioxidant activity, and more particularly to a peptide having radical-scavenging activity as well as functions of promoting the expression of Nrf2 as an antioxidant transcription factor and of promoting the expression of SOD2 as an antioxidant enzyme, and a composition containing the same.

BACKGROUND ART

In general, cells produce harmful oxygen such as reactive oxygen species (ROS) or free radicals upon largely exposure to stress caused by intrinsic factors (such as respiration and in-vivo energy metabolism) derived from biological processes and external factors (such as pollutants, toxic substances, ultraviolet rays, invasion of pathogens).

Normal cells remove the harmful oxygen with antioxidant enzymes through metabolic processes. However, continuous or severe stress results in accumulation of harmful oxygen in cells, rather than removal thereof, causing an inflammatory reaction or cell damage and then the onset of various diseases.

Furthermore, the harmful oxygen may cause DNA damage, protein denaturation, enzyme inactivation, and the like in cells, and lipid peroxide diffused into the cells or moved through the bloodstream promotes the production of new free radicals to facilitate arteriosclerosis, cancer, myocardial infarction, stroke, heart disease, rheumatoid arthritis, chronic neurodegenerative diseases such as amyotrophic lateral sclerosis or Parkinson's disease (PD), diabetes, hepatitis, nephritis, atopy, autoimmune diseases, inflammatory reactions, aging, and the like in various tissues (Alam, M. N. et al. Saudi Pharm. J. 2013; Curr. Opin. Neurol., 9(4):260-264, 1996).

In addition, such stress in cells is known to be a major cause of wrinkle formation or skin-associated diseases such as atopic dermatitis, acne or skin cancer, because it destroy cells, cuts connective tissues of the skin dermal layer, or causes cross-linking.

In response thereto, the human body has an antioxidant system that can remove free radicals, which are continuously produced, and cure damaged cells. For example, there is glutathione (GSH), to which three amino acids (L-glutamic acid, L-cysteine, and L-glycine) are bound. Glutathione is synthesized by glutamine cysteine ligase (GCL) and glutathione synthetase (GSS). Glutathione is known to exhibit antioxidant efficacy or remove toxic substances by repeatedly performing oxidation-reduction using the activity of antioxidant enzymes such as glutathione peroxidase (GPx), glutathione reductase (GR), glutathione S-transferase (GST), and quinone oxidoreductase (NADPH: quinone oxidoreductase 1 (NQO1)) (Mates, J M et al. Clinical biochemistry. 1999; Vrankovic, J. et al. Turkish Journal of Biology. 2012).

In addition, the main in-vivo biological defense mechanism against oxidative stress is based on the Nrf2 (nuclear factor erythroid 2-related factor 2)—ARE (antioxidant response element) signaling pathway present in cells, and the Nrf2-ARE signaling pathway promotes the synthesis of glutathione and antioxidant enzymes. The Nrf2 is a transcription factor which is known to function to remove reactive oxygen species by synthesizing antioxidant enzymes such as GPx, GR, GST, superoxide dismutase (SOD), catalase, NQO1, and heme oxygenase-1 (HO-1) in the presence of oxidative stress, or to increase the amount of glutathione in cells by regulating the expression of enzymes such as GCL and GS, which synthesize a glutathione antioxidant. As a result, reactive oxygen species are removed or converted to non-aggressive substances (Lee, J. M. et al. J. Biochem. Mol. Biol. 2004).

In addition, Nrf2 increases the viability of cells against free radicals in various tissues. Therefore, when the expression of Nrf2 is promoted in various tissues, an cytoprotective effect may be expected to be obtained based on antioxidation (Baird, L. et al. Arch. Toxicol. 2011).

The most important factor for efficiently maintaining the antioxidant defense mechanism in the human body is to normalize the production and reaction rate of SOD enzymes, which primarily neutralize superoxide anion radicals, which are the most powerful reactive oxygen species. However, the production and reaction rate of SOD enzymes in humans decrease with increasing age, so it is important to consume foods for supplementing the same. Among antioxidant enzymes, SOD plays an important role in the intracellular antioxidant defense system as an enzyme that reduces free radicals that are normally produced during the cellular energy metabolism. In mammals, SOD2 is also called "mitochondrial Mn-SOD".

However, the normal function of the human biological antioxidant system is gradually lost due to metabolic syndromes or adult diseases resulting from various factors including environmental stress such as pollution or ultraviolet radiation, or biological stress, aging and aging-related diseases such as degenerative diseases, economic growth, changes in diet, and the like. In this case, it is required to administer an antioxidant, in other words, a substance capable of removing active oxygen species by activating the Nrf2 electron factor, in order to supply an antioxidant to prevent malfunction of the antioxidant system. In response to this requirement for antioxidant administration, efforts to administer antioxidants or antioxidant foods and drugs to thereby prevent or treat the diseases described above or delay aging have been made in various ways. Antioxidants that are capable of satisfying these requirements have not been developed to date.

Against this background, as a result of repeated and intensive efforts to find food ingredients that exhibit antioxidant effects without causing any side effects, the present inventors identified that peptides have strong antioxidant effects based on the function of removing reactive oxygen species by promoting the expression of the transcription factor Nrf2, the function of removing reactive oxygen species by promoting the expression of the antioxidant enzyme SOD2, and the function of removing reactive oxygen species by promoting the expression of both Nrf2 and SOD2. Based on this finding, the present invention has been completed.

DISCLOSURE

Technical Problem

Therefore, the present invention has been made to solve the above problems, and it is one object of the present invention to provide a peptide that has no autoimmunity, is harmlessly degraded after biorecovery, and exhibits excellent antioxidant activity, thereby improving radical-scavenging ability, promoting the expression of Nrf2 and SOD2 when applied, and enhancing antioxidant activity. The peptide having antioxidant activity can be used as a therapeutic agent for diseases related to oxidative damage to cells, which has antioxidant activity against oxidative stress by effectively acting on biological tissues or cells thereof.

It is another object of the present invention to provide an antioxidant composition containing at least one peptide exhibiting antioxidant activity and having an amino acid sequence represented by General Formula 1 or 2, and a method for preparing the same.

It is another object of the present invention to provide a pharmaceutical composition or a pharmaceutical composition for application to animals other than humans for preventing, treating or ameliorating oxidative damage to cells containing the peptide as an active ingredient.

It is another object of the present invention to provide a method for preventing or treating oxidative damage to cells including orally administering the peptide to humans or animals other than humans.

It is another object of the present invention to provide novel use of the peptide for the preparation of a drug or a veterinary drug for preventing or treating oxidative damage to cells.

Technical Solution

In accordance with an aspect of the present invention, the above and other objects can be accomplished by the provision of an antioxidant composition containing a peptide exhibiting antioxidant activity and having an amino acid sequence represented by General Formula 1 or 2:

γ-Glu-Xaa¹         [General Formula 1]

γ-Glu-Xaa₂-Xaa³         [General Formula 2]

wherein

Xaa¹ is any one amino acid selected from alanine (A), cysteine (C), aspartic acid (D), glutamic acid (E), phenylalanine (F), glycine (G), histidine (H), isoleucine (I), leucine (L), asparagine (N), proline (P), glutamine (Q), arginine (R), threonine (T), valine (V), valine amide (V-NH2), valinol (2-amino-3-methyl-1-butanol) (V-ol), tryptophan (W), tyrosine (Y), ornithine (ORN), methionine sulfoxide (M(O)), cysteine in which hydrogen of a thiol group is substituted with a methyl group (C(S-Me)), cysteine in which hydrogen of a thiol group is substituted with a methyl group and which has a sulfoxide structure (S-Me) (O2), and 2-aminobutyric acid (Abu);

Xaa² is any one amino acid selected from cysteine (C), aspartic acid (D), glutamic acid (E), phenylalanine (F), glycine (G), histidine (H), isoleucine (I), leucine (L), asparagine (N), proline (P), glutamine (Q), arginine (R), serine (S), threonine (T), valine (V), valine amide (V-NH2), valinol (2-amino-3-methyl-1-butanol) (V-ol), tryptophan (W), tyrosine (Y), ornithine (ORN), methionine sulfoxide (M(O)), cysteine in which hydrogen of a thiol group is substituted with a methyl group (C(S-Me)), cysteine in which hydrogen of a thiol group is substituted with a methyl group (S-Me) (O2) and 2-amino butyric acid (Abu); and Xaa³ is any one amino acid selected from alanine (A), cysteine (C), aspartic acid (D), glutamic acid (E), phenylalanine (F), glycine (G), histidine (H), lysine (K), methionine (M), asparagine (N), proline (P), glutamine (Q), arginine (R), valine (V) and ornithine (ORN).

The peptide may include at least one peptide selected from the group consisting of γ-GLU-ALA, γ-GLU-CYS, γ-GLU-CYS(S-Me), γ-GLU-CYS(S-Me) (O2), γ-GLU-ASP, γ-GLU-GLU, γ-GLU-PHE, γ-GLU-GLY, γ-GLU-HIS, γ-GLU-ILE, γ-GLU-LEU, γ-GLU-MET(O), γ-GLU-ASN, γ-GLU-ORN, γ-GLU-PRO, γ-GLU-GLN, γ-GLU-ARG, γ-GLU-THR, γ-GLU-VAL, γ-GLU-VAL-NH2, γ-GLU-TRP, γ-GLU-TYR, γ-GLU-VAL-ol, γ-GLU-GLN-GLU, γ-GLU-GLU-GLU, γ-GLU-ILE-GLY, γ-GLU-PRO-GLY, γ-GLU-GLN-GLN, γ-GLU-SER-GLY, γ-GLU-THR-GLY, γ-GLU-VAL-GLY, γ-GLU-VAL-ALA, γ-GLU-VAL-CYS, γ-GLU-VAL-ASP, γ-GLU-VAL-GLU, γ-GLU-VAL-PHE, γ-GLU-VAL-HIS, γ-GLU-VAL-LYS, γ-GLU-VAL-MET, γ-GLU-VAL-ASN, γ-GLU-VAL-ORN, γ-GLU-VAL-PRO, γ-GLU-VAL-ARG, γ-GLU-VAL-VAL, γ-GLU-CYS(S-Me)-GLY, γ-GLU-Abu-GLY and γ-GLU-LEU-GLY.

The peptide may include at least one dipeptide selected from the group consisting of γ-GLU-ALA, γ-GLU-CYS, γ-GLU-CYS(S-Me), γ-GLU-CYS(S-Me) (O2), γ-GLU-GLY, γ-GLU-HIS, γ-GLU-ILE, γ-GLU-LEU, γ-GLU-ASN, γ-GLU-PRO, γ-GLU-GLN, γ-GLU-THR, γ-GLU-VAL-NH2, γ-GLU-TRP, γ-GLU-TYR and γ-GLU-VAL-ol.

The peptide may include at least one dipeptide selected from the group consisting of γ-GLU-CYS, γ-GLU-CYS(S-Me), γ-GLU-CYS(S-Me) (O2), γ-GLU-GLY, γ-GLU-HIS, γ-GLU-ILE, γ-GLU-GLN, γ-GLU-TRP and γ-GLU-TYR.

The peptide may include at least one tripeptide selected from the group consisting of γ-GLU-GLN-GLU, γ-GLU-ILE-GLY, γ-GLU-PRO-GLY, γ-GLU-SER-GLY γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN and γ-GLU-VAL-ARG.

The peptide may include at least one selected from the group consisting of γ-GLU-CYS(S-Me) (O2), γ-GLU-HIS, γ-GLU-CYS, γ-GLU-CYS(S-Me), γ-GLU-GLY, γ-GLU-ILE, γ-GLU-GLN, γ-GLU-TRP, γ-GLU-TYR, γ-GLU-GLN-GLU, γ-GLU-ILE-GLY, γ-GLU-PRO-GLY, γ-GLU-SER-GLY, γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN and γ-GLU-VAL-ARG.

The peptide may include at least one selected from the group consisting of γ-GLU-CYS(S-Me) (O2), γ-GLU-HIS, γ-GLU-ILE, γ-GLU-GLN-GLU, γ-GLU-THR-GLY, and γ-GLU-VAL-CYS.

In accordance with another aspect of the present invention, provided is a method for preparing an antioxidant composition, the method including:

a) adding an enzyme to a yeast suspension and conducting hydrolysis; and b) recovering a peptide fraction having a molecular weight of 500 Da or less from the yeast hydrolyzate obtained after hydrolysis.

The step a) may include: a-1) adding 0.5 to 1.5% by weight of Alcalase with respect to the solid content of the yeast suspension and conducting primary hydrolysis for 3 to 5 hours;
  a-2) adding 0.5 to 1.5% by weight of Flavourzyme with respect to the solid content of the primary hydrolyzate and conducting secondary hydrolysis for 5 to 15 hours; and
  a-3) adding 0.1 to 0.5% by weight of Alcalase and Flavourzyme with respect to the solid content of the secondary hydrolyzate, and conducting secondary hydrolysis for 20 to 30 hours.

In accordance with another aspect of the present invention, provided are a pharmaceutical composition, a food composition, a feed composition and a cosmetic composition for treating oxidative damage to cells containing the at least one peptide selected from amino acid sequences represented by General Formulas 1 and 2 as an active ingredient.

Oxidative damage to cells may be caused by the generation of free radicals or reactive oxygen species (ROS).

In accordance with another aspect of the present invention, provided is the use of at least one peptide selected from amino acid sequences represented by General Formulas 1 and 2 above for the preparation of a drug for preventing or treating oxidative damage to cells.

In accordance with another aspect of the present invention, provided is a method for treating oxidative damage to cells including orally administering the at least one peptide selected from amino acid sequences represented by General Formulas 1 and 2 above to humans or non-human animals.

The oxidative damage to cells may be caused by the generation of free radicals or reactive oxygen species (ROS).

Advantageous Effects

The present invention is directed to a functional peptide having excellent antioxidant activity, and is provided as a peptide having excellent biocompatibility and antioxidant activity remarkably superior to that of the conventional GSH in order to overcome low antioxidant activity, which is the limitation of the prior art. The peptide of the present invention effectively promotes recovery of damage to biological tissues or cells caused by free radicals resulting from oxidative stress, or promotes antioxidant activity. Therefore, such a peptide having antioxidant activity can be used to prevent and recover cell damage by effectively acting on cell damage caused by oxidative stress.

BEST MODE

Figure 1A:
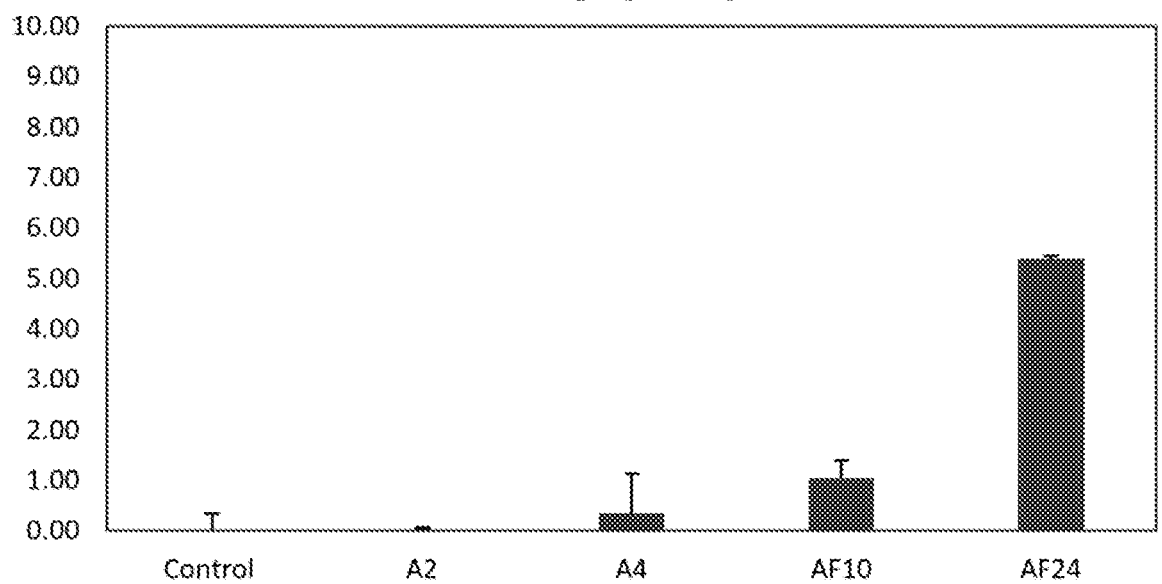
FIG. 1A is a graph showing DPPH-scavenging ability and FIG. 1B shows reducing power of respective yeast hydrolyzates (A4, AF10, AF24), wherein Control is a yeast hydrolyzate not treated with an enzyme, A2 is a yeast hydrolyzate lysed with Alcalase for 2 hours, A4 is a yeast hydrolyzate lysed with Alcalase for 4 hours, AF10 is a yeast hydrolyzate lysed with Alcalase for 4 hours and then lysed with Flavourzyme for 10 hours, and AF24 is a yeast hydrolyzate lysed with Alcalase for 4 hours, then lysed with Flavourzyme for 10 hours, and further lysed with Flavourzyme for 24 hours.

Hereinafter, the present invention will be described in detail.

Representative amino acids and abbreviations thereof are as follows: alanine (Ala, A), isoleucine (Ile, I), leucine (Leu, L), methionine (Met, M), phenylalanine (Phe, F), proline (Pro, P), tryptophan (Trp, W), valine (Val, V), asparagine (Asn, N), cysteine (Cys, C), glutamine (Gln, Q), glycine (Gly, G), serine (Ser, S), threonine (Thr, T), tyrosine (Try, Y), aspartic acid (Asp, D), glutamic acid (Glu, E), arginine (Arg, R), histidine (His, H), and lysine (Lys, K).

In addition, modified amino acids and abbreviations thereof are as follows: valine amide (V-NH2), valinol (2-amino-3-methyl-1-butanol) (V-ol), ornithine (ORN), methionine sulfoxide (M(O)), cysteine in which hydrogen of a thiol group is substituted with a methyl group (C(S-Me)), cysteine in which hydrogen of a thiol group is substituted with a methyl group and which has a sulfoxide structure (S-Me) (O2), and 2-aminobutyric acid (Abu). In particular, (O2) in formula above represents a sulfoxide structure.

In the present invention, a peptide refers to a linear molecule formed by mutual bonding between amino acid residues through a peptide bond.

The peptide of the present invention may be prepared in accordance with a chemical synthesis method, in particular, a solid-phase synthesis technique, which is known in the art (Merrifield, J. Amer. Chem. Soc. 85:2149-54(1963); Stewart et al., Solid Phase Peptide Synthesis, 2nd. ed., Pierce Chem. Co.: Rockford, 111(1984)).

As used herein, the term "antioxidant activity" refers to a property of inhibiting the oxidation of cells caused by highly reactive free radicals or reactive oxygen species upon exposure to oxidative stress due to environmental stress or biological stress such as intracellular metabolism or ultraviolet rays, and includes a property of removing free radicals or reactive oxygen species to reduce damage to cells resulting therefrom.

As used herein, the term "antioxidant composition" refers to a composition containing an antioxidant peptide in an amount of 20 to 50% by weight, preferably 30 to 40% by weight, with respect to the total weight of the composition, and the composition may further contain a pharmaceutically acceptable carrier, excipient or diluent, which will be obvious to those skilled in the art.

In one aspect, the present invention is directed to an antioxidant composition containing at least one peptide selected from amino acid sequences represented by the following General Formula 1 and 2:

γ-Glu-Xaa¹                             [General Formula 1]

γ-Glu-Xaa²-Xaa³                    [General Formula 2]

wherein

Xaa¹ is any one amino acid selected from alanine (A), cysteine (C), aspartic acid (D), glutamic acid (E), phenylalanine (F), glycine (G), histidine (H), isoleucine (I), leucine (L), asparagine (N), proline (P), glutamine (Q), arginine (R), serine (S) threonine (T), valine (V), valinol (2-amino-3-methyl-1-butanol) (V-ol), tryptophan (W), tyrosine (Y), ornithine (ORN), methionine sulfoxide (M(O)), cysteine in which hydrogen of a thiol group is substituted with a methyl group (C(S-Me)), cysteine in which hydrogen of a thiol group is substituted with a methyl group and which has a sulfoxide structure (S-Me) (O2), and 2-aminobutyric acid (Abu);

Xaa² is any one amino acid selected from cysteine (C), aspartic acid (D), glutamic acid (E), phenylalanine (F), glycine (G), histidine (H), isoleucine (I), leucine (L), asparagine (N), proline (P), glutamine (Q), arginine (R), serine (S), threonine (T), valine (V), valinol (2-amino-3-methyl-1-butanol) (V-ol), tryptophan (W), tyrosine (Y), ornithine (ORN), methionine sulfoxide (M(O)), cysteine in which hydrogen of a thiol group is substituted with a methyl group (C(S-Me)), cysteine in which hydrogen of a thiol group is substituted with a methyl group (S-Me) (O2) and 2-amino butyric acid (Abu); and Xaa³ is any one amino acid selected from alanine (A), cysteine (C), aspartic acid (D), glutamic acid (E), phenylalanine (F), glycine (G), histidine (H), lysine (K), methionine (M), asparagine (N), proline (P), glutamine (Q), arginine (R), valine (V) and ornithine (ORN).

In the present invention, the general formula is provided to illustrate the peptide structure of the present invention, and it will be obvious to those skilled in the art that modifications thereof also fall within the scope of the present invention.

In one embodiment, the N-terminus or C-terminus of the peptide of the present invention may be modified with a hydroxyl group (—OH) or an amino group (—NH₂). The modification of an amino acid may function to greatly improve the stability of the peptide of the present invention. Here, the term "stability" means in-vivo stability and storage stability (e.g., room-temperature storage stability). The protective group may function to protect the peptide according to the present invention from attacks by protein cleavage enzymes in vivo.

The peptide having antioxidant activity according to the present invention is obtained by obtaining yeast hydrolyzates through a series of enzymatic lysis steps, separating peptides from the yeast hydrolyzates by primary and secondary separation and purification, and then comparing the effects of promoting Nrf2 and SOD2 mRNA expression between the peptides. The peptides have higher Nrf2-mRNA- and SOD2-mRNA-promoting activity than natural GSH peptides, and exhibit remarkably excellent antioxidant effects (DPPH-scavenging ability, reducing power, Nrf2-mRNA-expression-promoting ability, and SOD2-mRNA-expression-promoting ability) despite having a short sequence (consisting of 2 to 3 amino acid residues), thus being useful in various fields requiring antioxidant activity.

Therefore, the peptide having antioxidant activity according to the present invention may be provided in the form of a composition for removing reactive oxygen species and preventing or treating oxidative damage to cells, tissues or organs caused by free radicals resulting from oxidative stress. In addition, the antioxidant composition may be provided as a feed, feed additive or food additive having an effect of preventing or treating cell damage caused by reactive oxygen species.

The peptide having an amino acid sequence represented by General Formula 1 or 2 according to the present invention is provided with a short sequence of 2 to 3 amino acids by sequentially binding amino acid residues to the gamma chain of L-glutamic acid.

Specifically, the peptide having amino acid sequence represented by General Formula 1 or 2 may have antioxidant activity and include at least one selected from the group consisting of γ-GLU-ALA, γ-GLU-CYS, γ-GLU-CYS(S-Me), γ-GLU-CYS(S-Me) (O2), γ-GLU-ASP, γ-GLU-GLU, γ-GLU-PHE, γ-GLU-GLY, γ-GLU-HIS, γ-GLU-ILE, γ-GLU-LEU, γ-GLU-MET(O), γ-GLU-ASN, γ-GLU-ORN, γ-GLU-PRO, γ-GLU-GLN, γ-GLU-ARG, γ-GLU-THR, γ-GLU-VAL, γ-GLU-VAL-NH2, γ-GLU-TRP, γ-GLU-TYR, γ-GLU-VAL-ol, γ-GLU-GLN-GLU, γ-GLU-ALA-GLY, γ-GLU-GLU-GLU, γ-GLU-ILE-GLY, γ-GLU-PRO-GLY, γ-GLU-GLN-GLN, γ-GLU-SER-GLY, γ-GLU-THR-GLY, γ-GLU-VAL-GLY, γ-GLU-VAL-ALA, γ-GLU-VAL-CYS, γ-GLU-VAL-ASP, γ-GLU-VAL-GLU, γ-GLU-VAL-PHE, γ-GLU-VAL-HIS, γ-GLU-VAL-LYS, γ-GLU-VAL-MET, γ-GLU-VAL-ASN, γ-GLU-VAL-ORN, γ-GLU-VAL-PRO, γ-GLU-VAL-ARG, γ-GLU-VAL-VAL, γ-GLU-CYS(S-Me)-GLY, γ-GLU-Abu-GLY and γ-GLU-LEU-GLY.

In one embodiment, the peptide is preferably a peptide of General Formula 1, wherein Xaa¹ is any one amino acid selected from alanine (A), cysteine (C), glycine (G), histidine (H), isoleucine (I), leucine (L), asparagine (N), proline (P), glutamine (Q), threonine (T), valine amide (V-NH2), valinol (2-amino-3-methyl-1-butanol) (V-ol), tryptophan (W), tyrosine (Y), cysteine in which hydrogen of a thiol group is substituted with a methyl group (C(S-Me)), and cysteine in which hydrogen of a thiol group is substituted with a methyl group and which has a sulfoxide structure (S-Me) (O2).

Specifically, the peptide of General Formula 1 may include at least one dipeptide selected from the group consisting of γ-GLU-ALA, γ-GLU-CYS, γ-GLU-CYS(S-Me), γ-GLU-CYS(S-Me) (O2), γ-GLU-GLY, γ-GLU-HIS, γ-GLU-ILE, γ-GLU-LEU, γ-GLU-ASN, γ-GLU-PRO, γ-GLU-GLN, γ-GLU-THR, γ-GLU-VAL-NH2, γ-GLU-TRP, γ-GLU-TYR and γ-GLU-VAL-ol, and has an antioxidant effect as well as effects of promoting the expression of Nrf2 mRNA and SOD2 mRNA, and has a comparable or superior effect despite having a shorter sequence than conventional GSH having an antioxidant effect, thus being still more useful in synthesis, preparation and storage.

More preferably, the peptide is a peptide of General Formula 1, wherein Xaa¹ is any one amino acid selected from cysteine (C), glycine (G), histidine (H), isoleucine (I), glutamine (Q), tryptophan (W), tyrosine (Y), cysteine in which hydrogen of a thiol group is substituted with a methyl group (C(S-Me)), and cysteine in which hydrogen of a thiol group is substituted with a methyl group and which has a sulfoxide structure (S-Me) (O2). The peptide has a significantly improved effect of promoting the expression of both Nrf2 and SOD2 compared to GSH, which is widely known to have an antioxidant effect and is specifically at least one dipeptide selected from the group consisting of γ-GLU-CYS, γ-GLU-CYS(S-Me), γ-GLU-CYS(S-Me) (O2), γ-GLU-GLY, γ-GLU-HIS, γ-GLU-ILE, γ-GLU-GLN, γ-GLU-TRP and γ-GLU-TYR.

In one embodiment, in the peptide of General Formula 2, $Xaa^2$ is any one amino acid selected from glycine (G), isoleucine (I), proline (P), serine (S), threonine (T) and valine (V), and $Xaa^3$ is any one amino acid selected from cysteine (C), aspartic acid (D), glutamic acid (E), phenylalanine (F), glycine (G), methionine (M), asparagine (N), and arginine (R). The peptide has a significantly improved effect of promoting the expression of both Nrf2 and SOD2 compared to GSH, and is specifically at least one tripeptide selected from the group consisting of γ-GLU-GLN-GLU, γ-GLU-ILE-GLY, γ-GLU-PRO-GLY, γ-GLU-SER-GLY γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN and γ-GLU-VAL-ARG.

In one embodiment, the peptide having a significantly improved effect of promoting the expression of both Nrf2 and SOD2 compared to GSH is more preferably characterized in that $Xaa^1$ in General Formula 1 is any one amino acid selected from cysteine (C), glycine (G), histidine (H), isoleucine (I), glutamine (Q), tryptophan (W), tyrosine (Y), cysteine in which hydrogen of a thiol group is substituted with a methyl group (C(S-Me)), and cysteine in which hydrogen of a thiol group is substituted with a methyl group and which has a sulfoxide structure (S-Me) (O2), and in General Formula 2, $Xaa^2$ is any one amino acid selected from isoleucine (I), proline (P), glutamine (G), serine (S), threonine (T) and valine (V), and $Xaa^3$ is any one amino acid selected from cysteine (C), aspartic acid (D), glutamic acid (E), phenylalanine (F), glycine (G), methionine (M), asparagine (N), and arginine (R). Specifically, the peptide preferably includes at least one selected from the group consisting of γ-GLU-CYS(S-Me) (O2), γ-GLU-HIS, γ-GLU-CYS, γ-GLU-CYS(S-Me), γ-GLU-GLY, γ-GLU-ILE, γ-GLU-GLN, γ-GLU-TRP, γ-GLU-TYR, γ-GLU-GLN-GLU, γ-GLU-ILE-GLY, γ-GLU-PRO-GLY, γ-GLU-SER-GLY, γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN and γ-GLU-VAL-ARG.

Most preferably, in General Formula 1, $Xaa^1$ is any one amino acid selected from histidine (H), isoleucine (I), and cysteine in which hydrogen of a thiol group is substituted with a methyl group and which has a sulfoxide structure (S-Me) (O2), and in General Formula 2, $Xaa^2$ is any one amino acid selected from glutamine (Q), threonine (T) and valine (V), and $Xaa^3$ is any one amino acid selected from cysteine (C), glutamic acid (E) and glycine (G).

Specifically, the peptide may include at least one peptide selected from the group consisting of γ-GLU-CYS(S-Me) (O2), γ-GLU-HIS, γ-GLU-ILE, γ-GLU-GLN-GLU, γ-GLU-THR-GLY, and γ-GLU-VAL-CYS. The peptide has antioxidant effects (reducing powder, DPPH-scavenging ability and Nrf2 mRNA activity), as well as effects of increasing the expression levels of Nrf2 mRNA and SOD2 mRNA about 2 to 3 times compared to that of GSH, a positive control.

Meanwhile, γ-GLU-HIS has a remarkable effect of increasing the expression levels of Nrf2 and SOD2 mRNA 2 to 8 times compared to that of GSH.

The antioxidant composition of the present invention may be used as a pharmaceutical composition, health food composition, feed, feed additive, cosmetic composition, or pharmaceutical composition for application to animals other than humans and the like.

The term "antioxidant activity" as used herein refers to a property of inhibiting the oxidation of cells caused by highly reactive free radicals or reactive oxygen species upon exposure to environmental stress or biological stress due to intracellular metabolism or oxidative stress due to external factor such as ultraviolet rays, and includes activity of removing free radicals or reactive oxygen species to reduce damage to cells resulting therefrom. The effect associated therewith was verified through in-vitro experiments.

The antioxidant composition is a composition containing an antioxidant peptide in an amount of 20 to 50% by weight, preferably 30 to 40% by weight with respect to the total weight of the composition, and the composition may further contain a pharmaceutically acceptable carrier, excipient or diluent, which will be obvious to those skilled in the art.

In another aspect, the present invention is directed to a method for preparing an antioxidant composition containing a peptide fraction, the method including:
  a) adding an enzyme to a yeast suspension and conducting hydrolysis; and
  b) recovering a peptide fraction having a molecular weight of 500 Da or less from the yeast hydrolyzate obtained after hydrolysis.

The step a) preferably includes: a-1) adding 0.5 to 1.5% by weight of Alcalase with respect to the solid content of the yeast suspension and conducting primary hydrolysis for 3 to 5 hours;
  a-2) adding 0.5 to 1.5% by weight of Flavourzyme with respect to the solid content of the primary hydrolyzate and conducting secondary hydrolysis for 5 to 15 hours; and
  a-3) adding 0.1 to 0.5% by weight of Alcalase and Flavourzyme with respect to the solid content of the secondary hydrolyzate and conducting secondary hydrolysis for 20 to 30 hours. When the yeast hydrolyzate is prepared through the method described above, a fraction containing a large amount of peptides with excellent antioxidant effect can be obtained.

The hydrolysis is preferably carried out at a temperature of 40 to 70° C. When hydrolysis is carried out at a temperature lower than 40° C., the hydrolysis does not proceed well and the secretion of antioxidant metabolites against physical stress cannot be sufficiently induced, so sufficient peptides cannot be obtained. When the temperature range exceeds 70° C., a problem of apoptosis may occur.

The pH during the hydrolysis is preferably 6 to 7.

In the step b), specifically, the yeast hydrolyzate obtained after hydrolysis is fractionated based on molecular weight to recover a peptide fraction having a molecular weight of 500 Da or less.

The method may further include, before the step (b), removing the residue from the yeast hydrolyzate, and the removal of the residue may be carried out by a known method of removing solids from mixtures such as centrifugation and filtration. Preferably, the method is centrifugation.

The method of the present invention may further include, before the step (b), inactivating the enzyme contained in the yeast hydrolyzate. The inactivation is performed before and/or after removing the residue, and is preferably carried out before step (b) by inactivating the enzyme contained in the yeast hydrolyzate, removing the residue by centrifugation, and separating the supernatant. The inactivation is preferably carried out by heat treatment and may be performed by maintaining the hydrolyzate at a temperature of 100° C. to 120° C. for 10 to 30 minutes.

In step (b), a peptide fraction having a molecular weight of 500 Da or less is obtained and the obtaining the fraction may be carried out by a known method of separating a substance based on molecular weight, for example, dialysis, electrophoresis, various kinds of column chromatography, and the like. The chromatography to remove undesired substances may be ion exchange chromatography, gel-penetration chromatography, HPLC, reverse-phase HPLC, affinity column chromatography, ultrafiltration, or a combination thereof. Preferably, the obtaining the fraction of the present invention may be carried out by a method of removing substances falling outside of a target molecular weight range by dialysis using a dialysis membrane.

The obtained fraction has a molecular weight of 1000 Da or less, and preferably a molecular weight of 100 Da to 700 Da. More preferably, the fraction may have a molecular weight of 500 Da or less.

In addition, the peptide having antioxidant activity may be present in an amount of 70 to 85% by weight with respect to the total weight of the obtained fraction.

In another aspect, the present invention is directed to a pharmaceutical composition for treating oxidative damage to cells containing at least one peptide selected from amino acid sequences represented by General Formulas 1 and 2 above as an active ingredient.

In another aspect, the present invention is directed to a pharmaceutical composition or a pharmaceutical composition for application to animals other than humans for preventing, treating or ameliorating oxidative damage to cells containing at least one peptide selected from amino acid sequences represented by General Formulas 1 and 2 above as an active ingredient.

In another aspect, the present invention is directed to a method for preventing or treating oxidative damage to cells including orally administering at least one peptide selected from amino acid sequences represented by General Formulas 1 and 2 above to humans or animals other than humans.

In another aspect, the present invention is directed to a novel use of the at least one peptide selected from amino acid sequences represented by General Formulas 1 and 2 above for the preparation of a drug or a veterinary drug for preventing or treating oxidative damage to cells.

As used herein, the term "oxidative damage to cells" refers to damage to cells resulting from highly reactive free radicals or reactive oxygen species produced upon exposure to environmental stress or biological stress due to intracellular metabolism or oxidative stress due to external factor such as ultraviolet rays.

As used herein, the term "containing as an active ingredient" means containing the peptide of the present invention in an amount sufficient to achieve an efficacy or activity of ameliorating, treating or preventing oxidative damage to cells.

As used herein, the term "prevention" may mean any action of inhibiting or delaying the onset of oxidative damage to cells by administering the composition according to the present invention to a subject. As used herein, the term "treatment" may mean any action of ameliorating or alleviating symptoms resulting from oxidative damage to cells by administering the composition according to the present invention to a subject suspected of having undergone oxidative damage to cells.

The type of disease caused by oxidative damage to cells that can be prevented or treated by the present invention is not limited, and is preferably a disease associated with damage to cells resulting from highly reactive free radicals or reactive oxygen species produced upon exposure to oxidative stress caused by internal or external factors such as intracellular metabolism or external factors such as ultraviolet rays.

The disease associated with oxidative damage to cells includes at least one selected from: neurodegenerative diseases selected from multiple sclerosis, Alzheimer's disease, Parkinson's disease, amyotrophic lateral sclerosis and muscular dystrophy; eye diseases such as retinopathy, macular degeneration, and cataracts; ischemic diseases such as myocardial infarction and cerebral infarction; inflammatory diseases selected from arthritis, vasculitis, glomerulonephritis and lupus erythematosus; and atherosclerosis.

In the present invention, the at least one peptide selected from the amino acid sequences represented by General Formulae 1 and 2 above is found to promote and improve the expression of Nrf2 mRNA and SOD2 mRNA, which are antioxidant defense mechanisms against cells that have undergone oxidative stress induced by treatment with tBHP (direct-acting oxidative stress-inducing agent. In addition, the peptide can remarkably increase the cell viability, reduced by tBHP. That is, the pharmaceutical composition of the present invention that is added was found to increase antioxidant enzyme activity, which suggests that the pharmaceutical composition induces the expression of antioxidants, basically, enzymes, to enable cell adaptation.

The at least one peptide selected from amino acid sequence represented by General Formulas 1 and 2 has remarkable advantages of increasing cellular antioxidant activity, inhibiting cell damage due to oxidative stress caused by internal or external factors, and being noncytotoxic and stable at the administered dose.

The "drug", "pharmaceutical composition for application to animals (veterinary pharmaceutical composition)", or "drug for application to animals (veterinary drug)" may further contain, in addition to the peptide as an active ingredient, an appropriate additive, carrier, excipient, or diluent commonly used in the preparation of pharmaceutical compositions. The pharmaceutically acceptable additive, carrier, excipient or diluent according to the present invention may be present in an amount of 0.1 to 90 parts by weight based on the total weight of the composition, but is not limited thereto.

The additive that can be used in the present invention may be starch, gelatinized starch, microcrystalline cellulose, povidone, colloidal silicon dioxide, calcium hydrogen phosphate, lactose, mannitol, taffy, gum arabic, pregelatinized starch, corn starch, powder cellulose, hydroxypropyl cellulose, opary, sodium starch glycolate, carnauba wax, synthetic aluminum silicate, stearic acid, magnesium stearate, aluminum stearate, calcium stearate, white sugar, dextrose, sorbitol, talc, or the like.

The term "carrier" refers to a compound that facilitates the delivery of the compound into cells or tissues. The term "diluent" refers to a compound that stabilizes the biologically active state of a target compound and is diluted in water dissolving the compound.

The carrier, excipient or diluent is not particularly limited, and may be, for example, lactose, glucose, sugar, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil or the like.

The amount of the drug, veterinary pharmaceutical composition or veterinary drug that is used may vary depending on the age, gender and weight of the patient or the animal in need of treatment, and will depend on the condition of the subject in need of treatment, the specific category or type of the disease to be treated, the administration route and the nature of the therapeutic agent that is used.

The pharmaceutical composition of the present invention may be administered in any one of various oral and parenteral formulations upon actual clinical administration. The formulations may be prepared using diluents or excipients such as fillers, extenders, binders, wetting agents, disintegrants and surfactants. Solid formulations for oral administration may include tablets, pills, powders, granules, capsules or the like, and may be prepared by mixing the peptide with at least one excipient, for example, starch, calcium carbonate, sucrose, lactose, or gelatin. In addition to simple excipients, lubricants such as magnesium stearate and talc may also be used. Liquid formulations for oral administration include suspensions, oral liquids and solutions, emulsions, syrups and the like. Liquid formulations may contain, in addition to water and liquid paraffin, which are commonly used simple diluents, various excipients such as wetting agents, sweeteners, fragrances and preservatives. Formulations for parenteral administration may include sterilized aqueous solutions, non-aqueous solvents, suspensions, emulsions, lyophilized formulations, and suppositories. As the non-aqueous solvents and suspensions, propylene glycol, polyethylene glycol, vegetable oils such as olive oil, and injectable esters such as ethyl oleate may be used. As a base for suppositories, Witepsol, macrogol, Tween 61, cacao butter, laurin paper, glycerogelatin, and the like may be used.

The pharmaceutical composition of the present invention may be administered orally or parenterally in accordance with a desired method, and the parenteral administration is preferably external application to the skin, intraperitoneal injection, rectal injection, subcutaneous injection, intravenous injection, intramuscular injection, or intrathoracic injection.

The dosage of the pharmaceutical composition of the present invention varies depending on the patient's weight, age, gender, state of health, diet, administration time, administration method, excretion rate, and severity of disease, the daily dosage is 0.0001 to 100 mg/kg, preferably 0.001 to 10 mg/kg, based on the amount of the peptide according to the present invention, and the pharmaceutical composition may be administered 1 to 6 times a day.

The pharmaceutical composition of the present invention may be used alone or in combination with surgery, radiation therapy, hormone therapy, chemotherapy, and methods using biological response modifiers.

The method of applying the pharmaceutical composition of the present invention is not particularly limited, and may be any invasive or non-invasive administration method, including oral administration, injection or the like, and may be suppository administration or transdermal administration. The active ingredient may be administered in the form of a conventional pharmaceutical preparation along with a solid or liquid pharmaceutical carrier suitable for administration methods such as oral administration and injection. Examples of such formulations include solid formulations such as tablets, granules, powders and capsules, liquid formulations such as solutions, suspensions and emulsions, and lyophilized formulations. These formulations may be prepared by conventional formulation methods. In addition, the pharmaceutical composition of the present invention may optionally contain any pharmaceutically or physiologically acceptable solid or liquid carrier, additive, or the like.

Examples of the carrier include glucose, lactose, sucrose, starch, mannitol, dextrin, fatty acid glyceride, polyethylene glycol, hydroxyethyl starch, ethylene glycol, polyoxyethylene sorbitan fatty acid ester, gelatin, albumin, amino acids, water, physiological saline and the like. Further, if necessary, conventional additives such as stabilizers, wetting agents, emulsifiers, binders and isotonic agents may be appropriately added to the pharmaceutical composition of the present invention.

The treatment method includes administering the composition orally or parenterally to humans or animals other than humans, particularly mammals, for example, orally administering the composition to subjects in need of treatment in which cell damage is caused by internal or external oxidative stress or in which cell damage is induced by other factors.

The dosage, administration method and administration for the treatment may be determined with reference to the dosage, administration method, and number of administrations of the pharmaceutical composition, drug, veterinary pharmaceutical composition, or veterinary drug.

In another aspect, the present invention is directed to an antioxidant food composition containing the at least one peptide selected from amino acid sequences represented by General Formulas 1 and 2 above as an active ingredient.

The food composition may be prepared in the formulation of a capsule, tablet, powder, granule, liquid, pill, flake, paste, syrup, gel, jelly or bar using the peptide. Alternatively, a general food may be prepared by adding the food composition to a food material of a beverage, tea, spice, gum, confectionery or the like. The food has a specific effect on health when consumed, but has an advantage of being free of side effects which may occur when administering a drug for a long time, due to the use of food as a raw material, unlike general drugs.

The food composition is very useful because it can be consumed on a daily basis. The amount of the peptide that may be added to such a food composition is generally 0.01 to 50% by weight, preferably 0.1 to 20% by weight, based on the target food, without changing the original taste of the food, although the amount of the peptide cannot be uniformly defined with respect to the type of the target food. In addition, the food provided in the form of a capsule, tablet, powder, granule, liquid, pill, flake, paste, syrup, gel, jelly or bar is generally added in an amount of 0.1 to 100% by weight, preferably 0.5 to 80% by weight.

The food composition may contain at least one peptide represented by General Formula 1 or 2 above as an active ingredient, as well as ingredients commonly added for food production, for example, proteins, carbohydrates, fats, nutrients, seasonings and flavoring agents. Examples of the carbohydrates include: monosaccharides such as glucose and fructose; disaccharides such as maltose, sucrose and oligosaccharides; and polysaccharides, for example, common sugars such as dextrin and cyclodextrin and sugar alcohols such as xylitol, sorbitol, and erythritol.

As flavoring agents, natural flavoring agents [thaumatin, stevia extract (e.g., rebaudioside A and glycyrrhizin]) and synthetic flavoring agents (e.g., saccharin and aspartame) may be used. For example, when the food composition of the present invention is produced in the form of drinks and beverages, it may contain, in addition to the peptide of the present invention, citric acid, liquid fructose, sugar, glucose, acetic acid, malic acid, fruit juice, various plant extracts and the like.

The food composition of the present invention includes human food, beverages, and animal feed and feed additives.

Further, in the animal feed additive containing as an active ingredient the at least one peptide represented by General Formula 1 or 2 obtained by the present invention, the peptide includes polysaccharides and is produced in a powder form to produce an animal feed additive that is additionally added to animal feed. At this time, the animal feed may be selected from the group consisting of powdered animal feed, calf milk replacers and piglet creep feed, and the content of the peptide based on the dry weight ranges from 1 to 2 g (about 0.1%) with respect to 1 kg of the feed.

The food and health food composition of the present invention may contain the peptide of the present invention alone or in combination with other food or food ingredients, and may be appropriately used according to a conventional method.

In another aspect, the present invention is directed to an antioxidant cosmetic composition containing the at least one peptide selected from amino acid sequences represented by General Formulas 1 and 2 as an active ingredient.

The antioxidant cosmetic composition may have a formulation selected from the group consisting of an ointment for external application to the skin, cream, soft lotion, nutrient lotion, pack, essence, hair tonic, shampoo, rinse, hair conditioner, hair treatment, gel, skin lotion, skin softener, skin toner, astringent, lotion, milk lotion, moisture lotion, nutrition lotion, massage cream, nutrition cream, eye cream, moisture cream, hand cream, mask pack, foundation, nutrition essence, sunscreen, soap, cleansing foam, cleansing lotion, cleansing cream, body lotion and body cleanser, but is not limited thereto. The composition of each formulation may contain various bases and additives necessary and appropriate for the preparation of the formulation, and the types and amounts of these components can be easily selected by those skilled in the art.

When the formulation of the present invention is a paste, cream or gel, animal fiber, plant fiber, wax, paraffin, starch, tragacanth, cellulose derivative, polyethylene glycol, silicone, bentonite, silica, talc, or zinc acid may be used as a carrier component.

When the formulation of the present invention is a powder or spray, lactose, talc, silica, aluminum hydroxide, calcium silicate, or polyamide powder may be used as a carrier component. In particular, when the formulation is in the form of a spray, a propellant such as chlorofluorohydrocarbon, propane/butane, or dimethyl ether may be further contained.

When the formulation of the present invention is a solution or emulsion, a solvent, a solvating agent or an emulsifying agent, such as water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid ester of sorbitan, is used as a carrier component.

When the formulation of the present invention is in the form of a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth or the like may be used as a carrier component.

When the formulation of the present invention is in the form of a surfactant-containing cleanser, aliphatic alcohol sulfate, aliphatic alcohol ether sulfate, sulfosuccinic acid monoester, isethionate, an imidazolinium derivative, methyltaurate, sarcosinate, fatty acid amide ether sulfate, alkylamidobetaine, fatty alcohol, fatty acid glyceride, fatty acid diethanolamide, vegetable oil, a lanolin derivative, or ethoxylated glycerol fatty acid ester may be used as a carrier component.

MODE FOR INVENTION

Hereinafter, the present invention will be described in more detail with reference to preferred examples. However, it will be obvious to those skilled in the art that the following examples are provided only for illustration of the present invention and should not be construed as limiting the scope of the present invention.

Experimental Example 1. Screening of Low Molecular Weight Peptides Having Antioxidant Activity from Yeast Hydrolysates 1. Preparation of Yeast Hydrolyzate Yeast (*Saccharomyces cerevisiae*) cells were adjusted to pH 7.0 and heated to 60° C., and endopeptidase (Alcalase) was added in an amount of 1% with respect to solid content, followed by enzymatic lysis for 2 or 4 hours ("A2" or "A4" sample). After adding 1% of exopeptidase (Flavourzyme) to the sample (A4) lysed with Alcalase, compared to the solid content, enzymatic lysis was performed for 10 hours ("AF10" sample). After lysis for a total of 10 hours, 0.125% of Alcalase and Flavourzyme with respect to the solid content were added thereto at 55° C., followed by enzymatic lysis for 24 hours ("AF24" sample). The lysed supernatant was inactivated at 85° C. for 30 minutes, and a peptide having a molecular weight of less than 10 kDa was separated through an ultrafiltration process. The Alcalase and Flavourzyme used herein were purchased from Novozymes.

The antioxidant efficacy (DPPH) and reducing power of each of the yeast hydrolysates (A4, AF10, AF24) were measured.

2. DPPH (2,2-Diphenyl-1-Picryl-Hydrazyl-Hydrate) Assay Method

The antioxidant activity due to the DPPH-scavenging ability of yeast hydrolyzates was measured using the methods of Choi Chang-seop et al. (2003) and Shekhar et al. (2014). 20 µl of a sample (1 to 5000 µg/ml) dissolved in distilled water was added to 180 µl of an ethanol solution containing DPPH (0.111 mM). The resulting mixture was allowed to react at 25° C. for 30 minutes, and absorbance was measured at 517 nm. Ascorbic acid was used to create the standard curve, and DPPH-scavenging ability (%) was calculated and expressed by the equation of [(absorbance upon no addition of sample−absorbance of sample)/absorbance upon no addition of sample]×100.

3. Reducing Power Assay Method

The reducing power of yeast hydrolysates was measured using the method of Oyaizu (1986). Specifically, a sample (1-5000 µg/ml, 60 µl) dissolved in distilled water was mixed with phosphate buffer (150 µl, 0.2M, pH 6.6) and potassium ferricyanide (K 3 Fe(CN) 6, 150 µl, 1%), followed by reacting at 50° C. for 20 minutes. Further, 150 µl of trichloroacetic acid (10%) was added thereto, followed by centrifugation at 2,000 g for 10 minutes. 150 µl of the supernatant containing the sample was added to 150 µl of DW and $FeCl_3$ (30 µl, 0.1%). The resulting mixture was allowed to react at 25° C. for 10 minutes, and absorbance was measured at 700 nm.

4. Conclusion

Figure 1B:
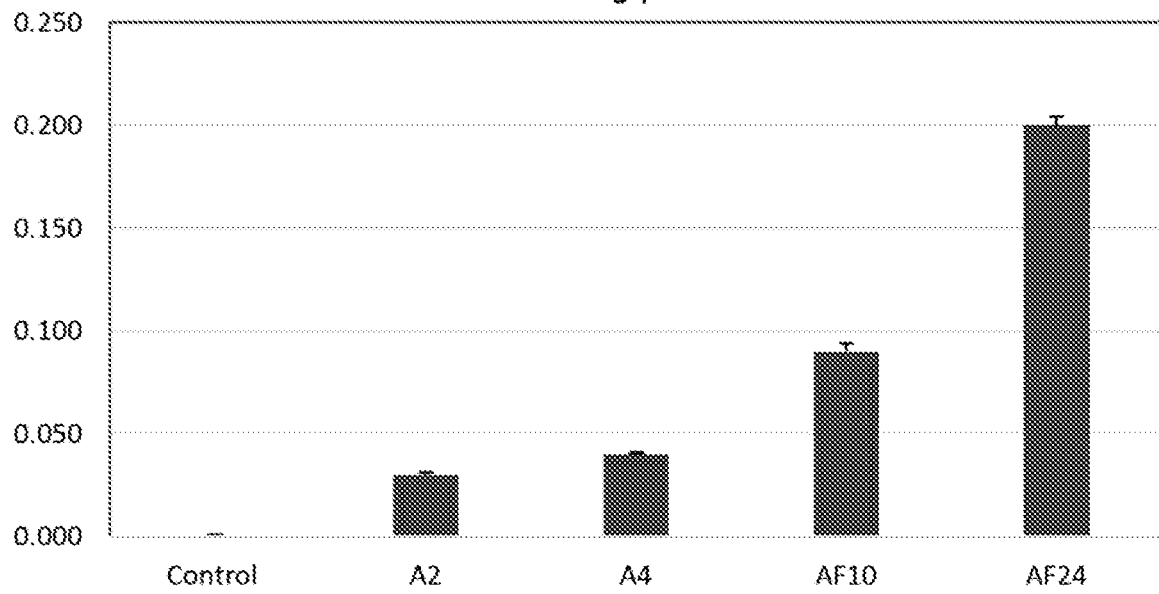

FIG. 1A is a graph showing the DPPH-scavenging ability and FIG. 1B shows reducing power (b) of respective yeast hydrolyzates (A4, AF10 and AF24), wherein Control is a yeast hydrolyzate not treated with an enzyme, A2 is a yeast hydrolyzate lysed with Alcalase for 2 hours, A4 is a yeast hydrolyzate lysed with Alcalase for 4 hours, AF10 is a yeast hydrolyzate lysed with Alcalase for 4 hours and then lysed with Flavourzyme for 10 hours, and AF24 is a yeast hydrolyzate lysed with Alcalase for 4 hours, then lysed with Flavourzyme for 10 hours, and further lysed with Flavourzyme for 24 hours.

As shown in FIGS. 1A and 1B, it was found that the sample of AF24 that was sequentially treated with Alcalase and Flavourzyme and lysed in multiple stages exhibited the best DPPH-scavenging ability and reducing power. That is, it can be seen that the DPPH-scavenging ability (FIG. 1A) and reducing power (FIG. 1B) of the same yeast hydrolyzate may differ depending on the enzyme and time. Therefore, in the present invention, the AF24 sample was used for screening for peptides having antioxidant effects.

Experimental Example 2. Primary Separation Depending on Molecular Weight of Yeast Hydrolyzate and Analysis of Antioxidant Activity of Each Fraction In Order to Separate and Select Peptides Having Excellent antioxidant activity from the AF24 sample, having the best antioxidant activity among the yeast hydrolysates, fractions were prepared from the AF24 yeast hydrolyzate based on the molecular weight (size) thereof, and the oxidation efficacy (DPPH) and reducing power thereof were measured and compared.

1. Preparation of Yeast Hydrolyzate Fraction

Specifically, the AF24 yeast hydrolyzate was filtered through ultrafiltration membranes with sizes of 10 kDa, 5 kDa and 1 kDa, moisture was removed from the filtrate of each fraction at 105° C. for 48 hours, and the dry weight was measured to obtain the content as shown in Table 1 below. As can be seen from Table 1, most of the fractions of the yeast hydrolyzate are substances having a size of 1 kDa or less.

TABLE 1

| Item | Molecular weight of yeast fraction (Dalton) | Content (%) |
| --- | --- | --- |
| Preparation Example 1 | 10,000 or more | 0.3 |
| Preparation Example 2 | 10,000~5,000 | 1.2 |
| Preparation Example 3 | 5,000~1,000 | 15.2 |
| Preparation Example 4 | 1,000 or less | 83.3 |

2. Experiment on Antioxidant Activity of Fractions of Yeast Hydrolyzate Based on Molecular Weight (Size)

The DPPH-scavenging ability and reducing power of the fractions of respective yeast hydrolyzates (Preparation Examples 1 to 4) were measured using the same method of measuring DPPH-scavenging ability and reducing power as in Experimental Example 1.

Figure 2A:
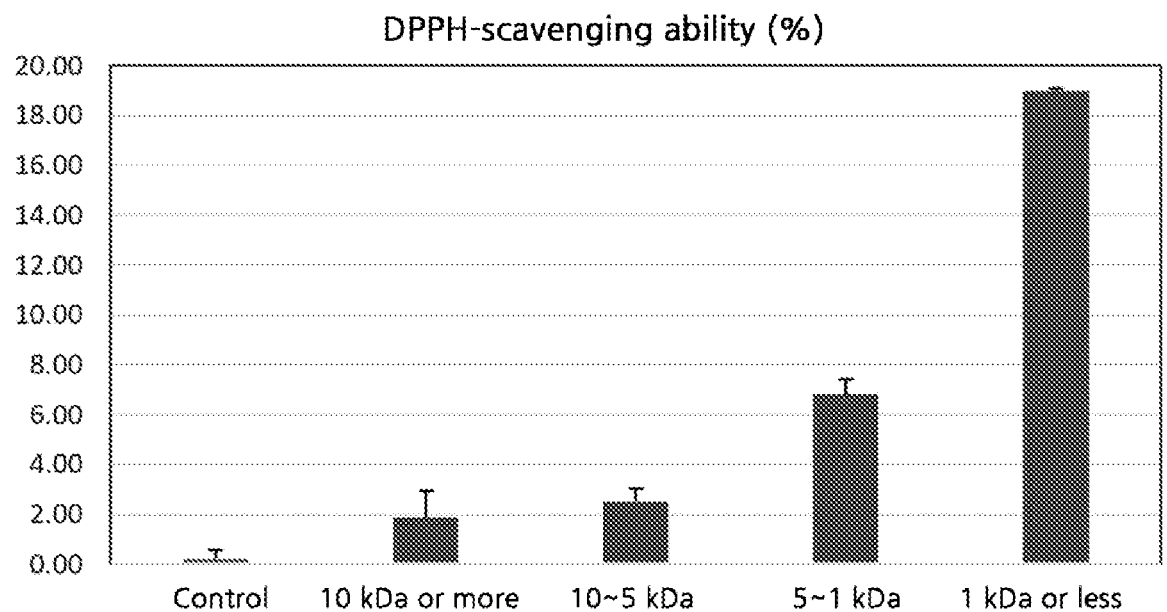
FIG. 2A is a graph showing DPPH-scavenging ability and FIG. 2B shows reducing power of respective yeast hydrolyzate fractions (Preparation Examples 1 to 4), wherein Control is a yeast hydrolyzate not treated with an enzyme, 10 kDa or more is a fraction of the yeast hydrolyzate of Preparation Example 1, 10 to 5 kDa is a fraction of the yeast hydrolyzate of Preparation Example 2, 5 to 1 kDa is a fraction of the yeast hydrolyzate of Preparation Example 3, and 1 kDa or less is a fraction of the yeast hydrolyzate of Preparation Example 4.
Figure 2B:
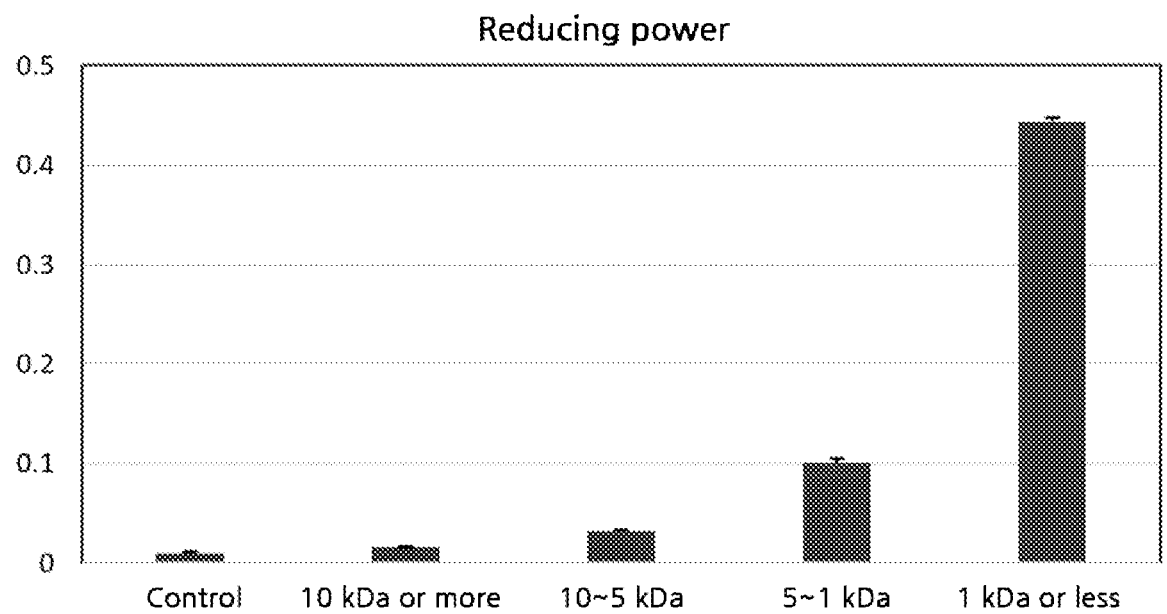

FIG. 2A is a graph showing the DPPH-scavenging ability and FIG. 2B shows reducing power (b) of respective yeast hydrolyzate fractions (Preparation Examples 1 to 4), wherein Control is a yeast hydrolyzate not treated with an enzyme, 10 kDa or more is a fraction of the yeast hydrolyzate of Preparation Example 1, 10 to 5 kDa is a fraction of the yeast hydrolyzate of Preparation Example 2, 5 to 1 kDa is a fraction of the yeast hydrolyzate of Preparation Example 3, and 1 kDa or less is a fraction of the yeast hydrolyzate of Preparation Example 4.

As can be seen from FIGS. 2A and 2B, the fraction of 5 kDa or less exhibits a DPPH-scavenging ability of 6% or more, and the fraction of 1 kDa or less (Preparation Example 4) exhibits the highest antioxidant activity, specifically 3 to 8 times higher antioxidant activity. It can be seen that, similar to DPPH-scavenging ability, the fraction of 1 kDa or less (Preparation Example 4) also exhibits remarkably superior reducing power (antioxidant activity) specifically, 4 times or more higher reducing power (antioxidant activity). Accordingly, in the present invention, the yeast hydrolyzate filtrate of 1 kDa or less was selected for screening peptides having an antioxidant effect.

Experimental Example 3. Secondary Separation of Filtrate of Yeast Hydrolyzate of 1 kDa or Less Depending on Molecular Weight After secondary separation depending on molecular weight of yeast hydrolyzate filtrate of 1 kDa or less, antioxidant activity was measured to select a final sample for screening peptides having antioxidant activity.

1. HPLC Analysis

The molecular weight distribution of the yeast hydrolyzate filtrate of 1 kDa or less selected in Experimental Example 2 was determined, and secondary separation was performed based on the molecular weight distribution. For this purpose, the molecular weight distribution of the yeast hydrolyzate filtrate with 1 kDa or less was detected using high-performance liquid chromatography (HPLC, Agilent 1200 series) and GPC method system software. The HPLC conditions therefor are shown in Table 2 below.

Specifically, HPCL was performed at a flow rate of 1 ml per minute for a total of 20 minutes after injecting 10 μl of a yeast hydrolyzate filtrate of 1 kDa or less into an Agilent PL aquagel-OH 20 column. The mobile phase used herein was a mixture of water, acetonitrile and trifluoroacetic acid in a ratio of 50:50:0.1, and the sample was detected at a wavelength of 220 nm.

TABLE 2

| Column | Agilent PL aquagel-OH 20 (5 μm, 7.5 mm ID × 300 mm L) |
| --- | --- |
| Mobile phase | water:CH$_3$CN:TFA = 50:50:0.1 |
| Injection volume | 10 μl |
| Flow rate | 1.0 ml/min |
| Wavelength | 220 nm |

2. Conclusion

Figure 3:
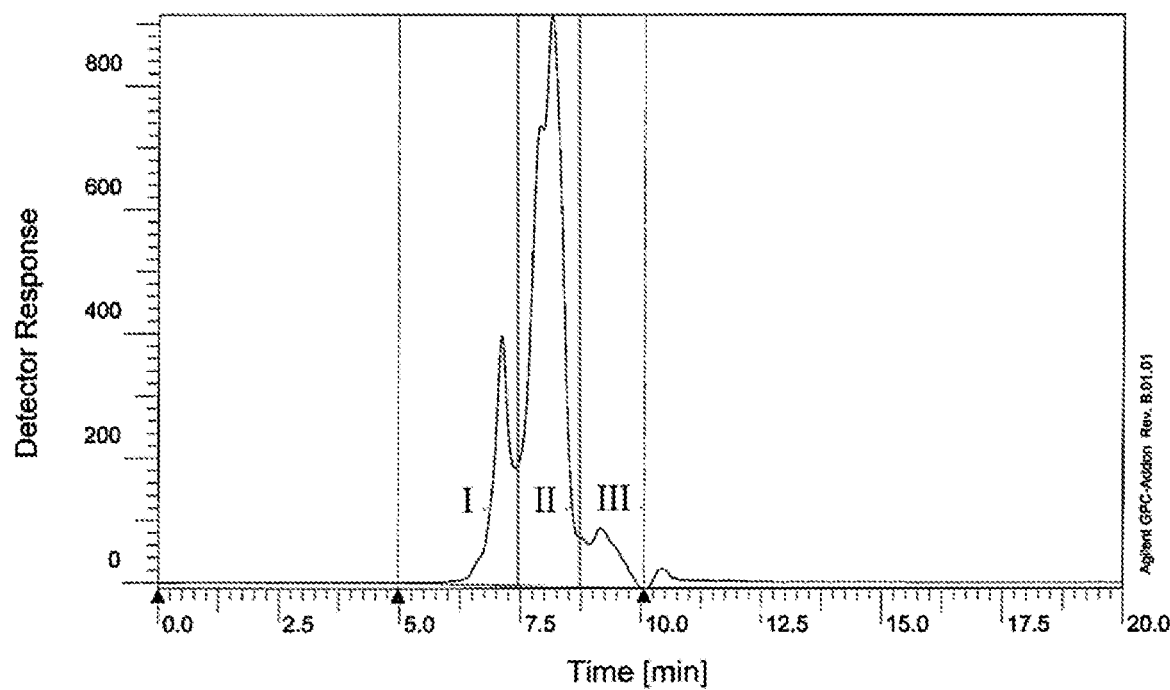
FIG. 3 is a graph showing the secondary fraction (I, II and III) depending on molecular weight determined based on the molecular weight distribution of the filtrate of yeast hydrolyzate of 1 kDa or less, selected from Experimental Example 2 using high performance liquid chromatography (HPLC) to screen peptides having antioxidant activity.
Figure 4A:
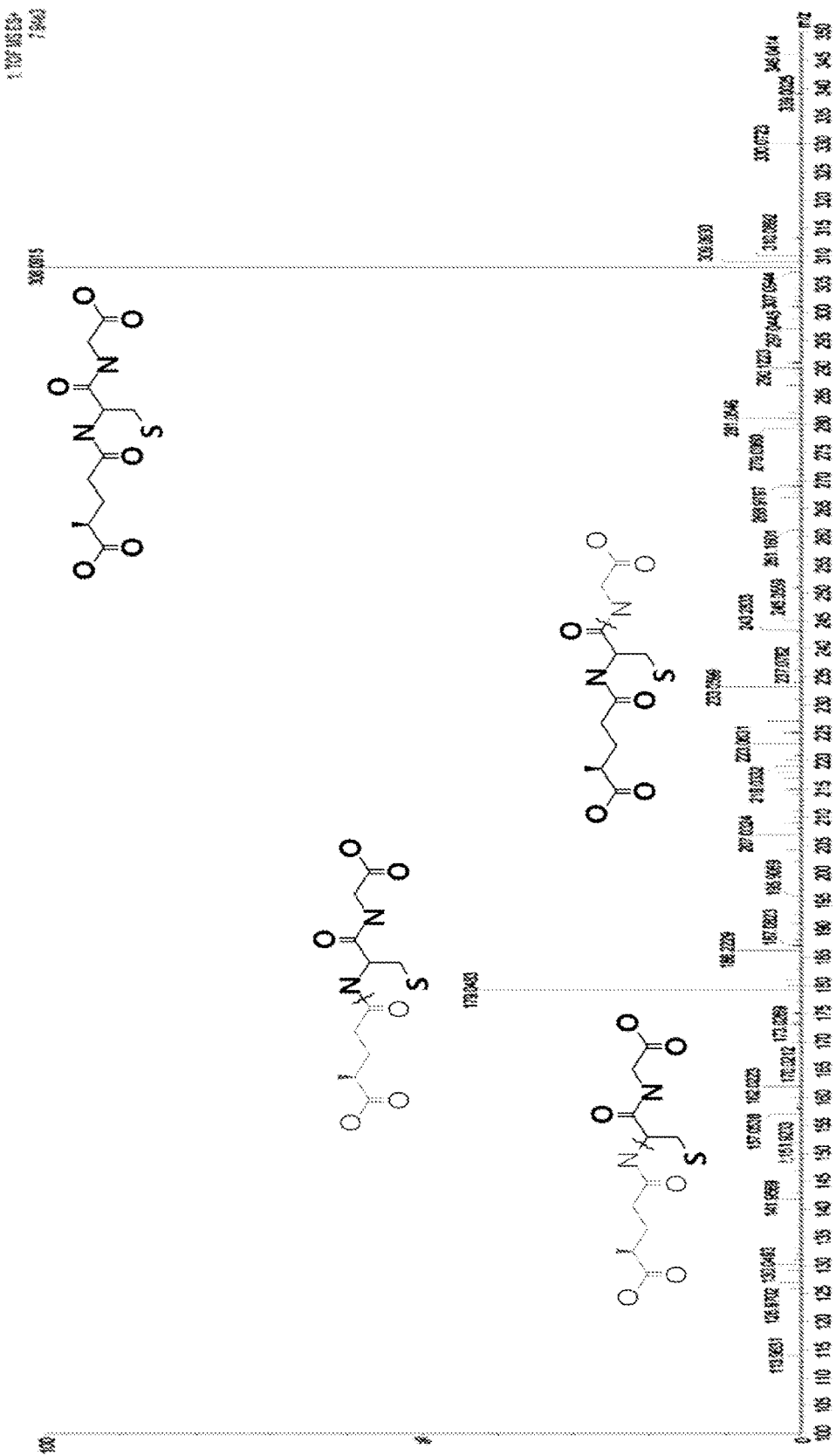
FIGS. 4A to 4D are graphs showing MS/MS spectra and predicted structures of representative peptides identified from the secondary fraction II having the best antioxidant activity from yeast hydrolyzates, wherein A is γ-Glu-Cys-Gly (GSH), B is γ-Glu-Val-Gly, C is γ-Glu-Cys, and D is γ-Glu-Val.
Figure 4B:
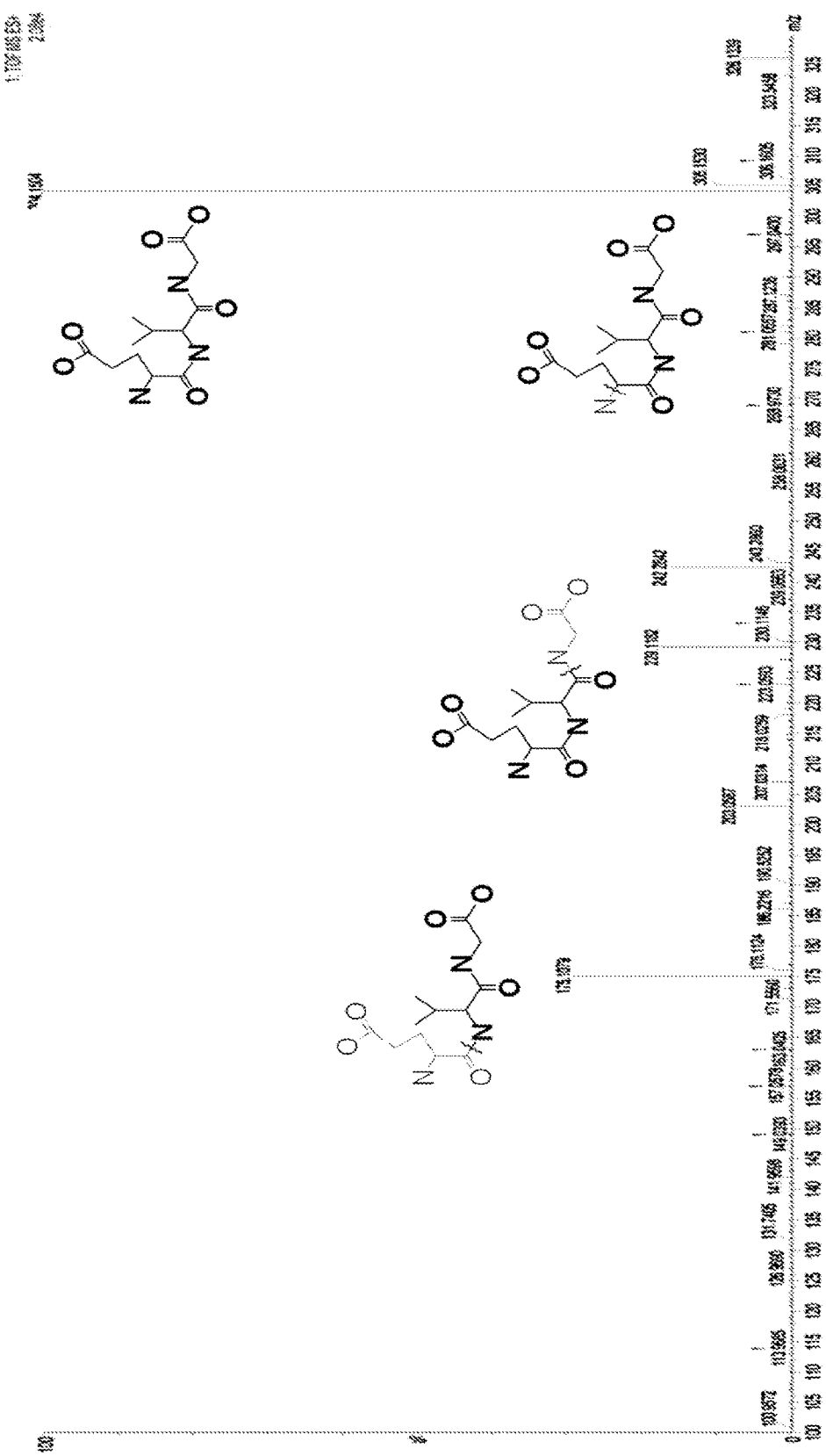
Figure 4C:
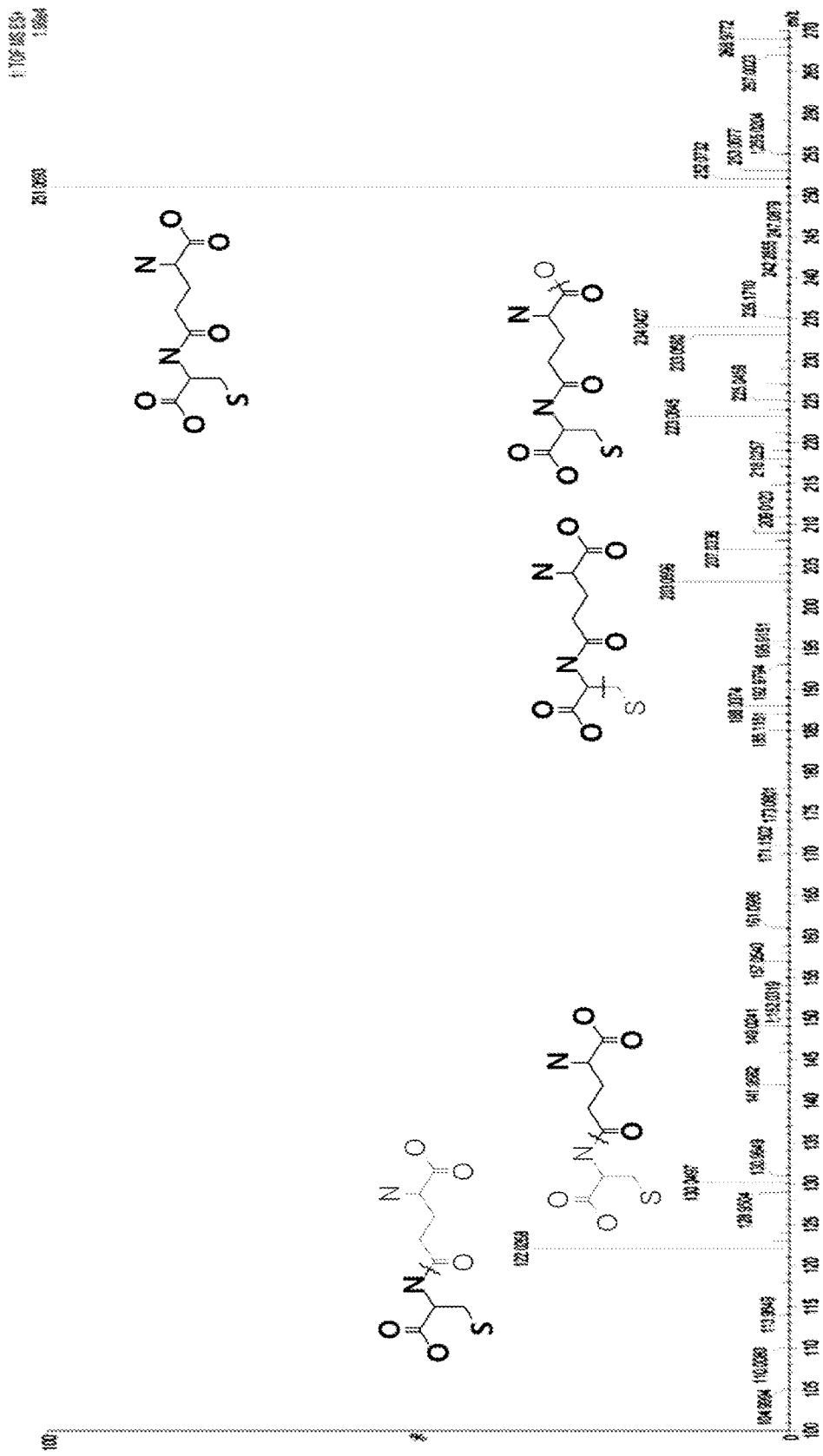
Figure 4D:
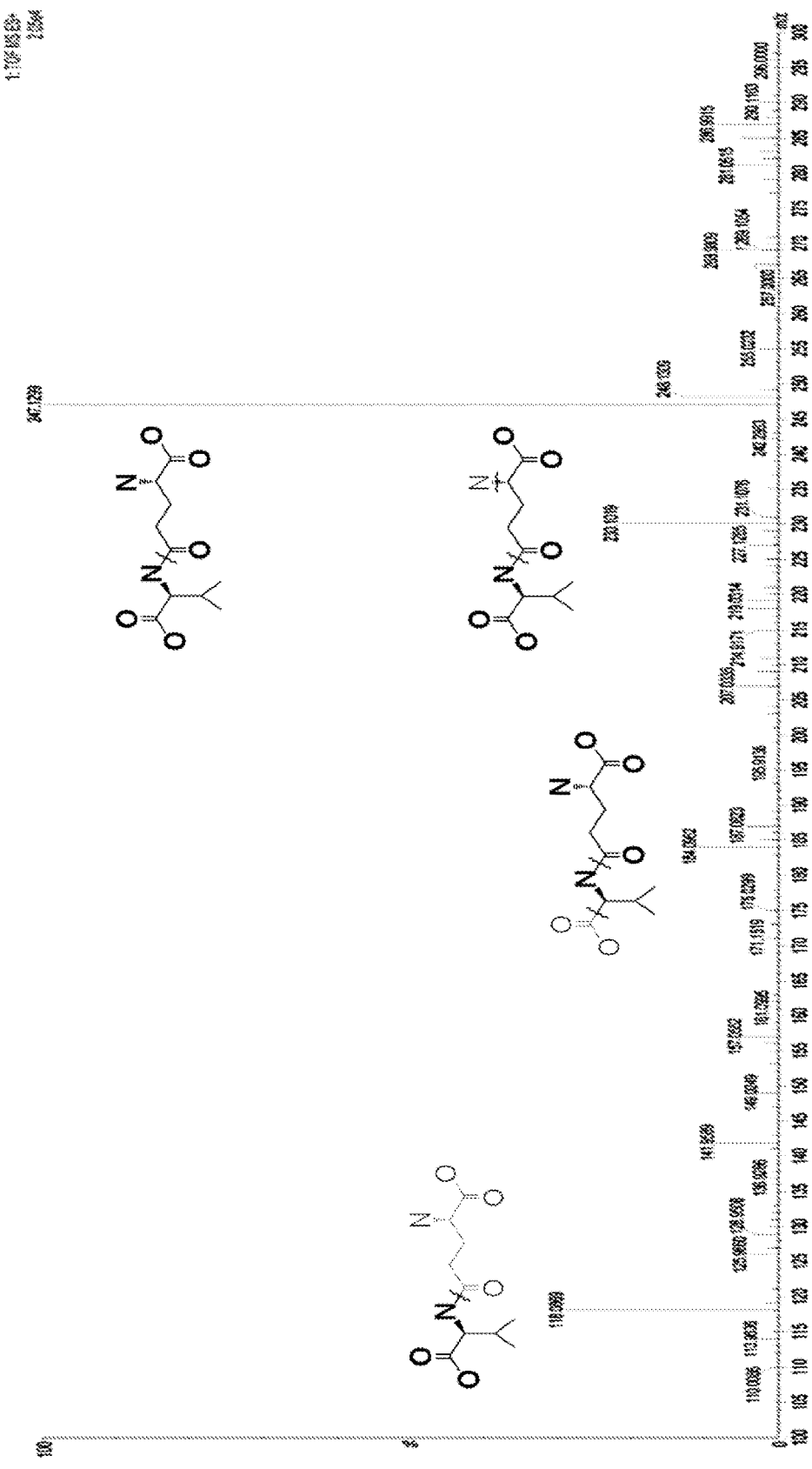

FIG. 3 is a graph showing the secondary fractions (I, II and III) obtained depending on molecular weight based on the molecular weight distribution of the yeast hydrolyzate filtrate of 1 kDa or less selected in Experimental Example 2, detected using high-performance liquid chromatography (HPLC) to screen peptides having antioxidant activity.

As shown in FIG. 3, the yeast hydrolyzate filtrate of 1 kDa or less selected in Experimental Example 2 had a total molecular weight of 1 kDa (1,000 dalton) or less. It was found that the yeast hydrolyzate filtrate contains 15.1% of peptides having a molecular weight of 500 daltons or more (secondary fraction I), 81.9% of peptides having a molecular weight of 500 daltons or less (secondary fraction II), and 3.0% of amino acids (secondary fraction III). Therefore, the secondary fraction II having the most antioxidant activity was finally selected for screening peptides having antioxidant activity, and the peptides were identified from the secondary fraction II.

Experimental Example 4. Identification of 100 Types of Peptides Having Antioxidant Activity from Secondary Fraction II In order to screen antioxidant functional peptides from the finally selected secondary fraction II, the peptides present in the secondary fraction II were identified, and the antioxidant activity was compared therebetween.

1. Peptide Identification

A mass spectrometer LC MS/MS system (Waters, USA) was used to analyze the amino acid sequences of the peptides, and the conditions and methods therefor are shown in Table 3 below.

Specifically, 5 µl of the finally selected secondary fraction II was injected into an LC MS/MS system and separated using a BEH C4 column. 100% solvent A as a mobile phase was injected for 1 minute at a flow rate of 0.2 ml/min, and then the solvent A was adjusted from 100% to 99% over 9 minutes. Then, the solvent A was reduced from 99% to 0% for 0.5 minutes, and the solvent A was again adjusted to 100% for the last 4.5 minutes. Mass spectrum analysis was performed using electrospray ionization in the positive mode within the range from 50 to 1,200 m/z. Operation coefficients thereof are as follows: ion source temperature: 120° C.; desolvation temperature: 400° C.; and sample analysis was performed using MassLynx 4.1 software (Waters, USA).

TABLE 3

| Column | BEH C4 (100 × 2.1 mm, 1.7 µm) | | |
|---|---|---|---|
| Solvent | A: 0.1% formic acid in water | | |
| | B: 0.1% formic acid in acetonitrile | | |
| Gradient conditions | Time (min) | A (%) | B (%) |
| | Initial | 100 | 0 |
| | 1.0 | 100 | 0 |
| | 10.0 | 99 | 1 |
| | 10.5 | 0 | 100 |
| | 15.0 | 100 | 0 |
| Column flow rate | 0.2 ml/min | | |
| Ionization mode | ESI positive mode | | |
| Source Temperature | 120° C. | | |
| Desolvation Temperature | 400° C. | | |

2. Conclusion

FIGS. 4A to 4D are graphs showing MS/MS spectra and predicted structures of representative peptides identified from the secondary fraction II having the best antioxidant activity from yeast hydrolyzates, wherein A is γ-Glu-Cys-Gly (GSH), B is γ-Glu-Val-Gly, C is γ-Glu-Cys, and D is γ-Glu-Val.

As shown in FIGS. 4A to 4D, the result showed that a total of 100 types of peptides were identified in the secondary fraction II, having the best antioxidant activity, obtained from the yeast hydrolyzate.

Experimental Example 5. Comparison in Nrf2 mRNA Expression Levels Between 100 Types of Peptides 1. Synthesis of 100 Types of Peptides The identified 100 types of peptides were prepared using a solid-phase synthesis technique and analyzed using an LC-MS/MS mass spectrometer system (Waters, USA). Then, in order to accurately determine whether or not each synthesized peptide has the same structure as each identified and designed peptide, the molecular weight was extracted in XIC mode based on the mono-isotope value (1.0 ppm or less) of a peptide indicator material, and two or more product ions were found to correspond on the MS/MS phase. All samples and indicators were measured in full scan and positive mode.

2. Analysis of Antioxidant Activity (Nrf2 mRNA Expression Level) of 100 Types of Peptides In the present invention, the antioxidant activity was compared between the 100 types of peptides, and the change in Nrf2 mRNA expression was measured through PCR in order to select the final peptide.

(1) Cell Culture and Treatment with 100 Types of Peptides

An HEK293 cell (kidney cell) line was seeded at a density of $6.6 \times 10^5$/well in DMEM (Dulbecco's Modified Eagle's Medium) medium on a 6-well plate and cultured at 37° C. under 5% $CO_2$ for 24 hours. The next day, the medium was exchanged with serum and amino-acid-free media, and then the cells were further cultured for 20 hours or longer. The cells were treated with Tert-BHP (300 µM) and 500 µM 100 types of peptides, and then cultured for 18 hours.

(2) RNA Extraction

RNA was extracted from the cells treated with 100 types of peptides in (1) using TRIzol (Thermo Fisher Scientific). A GoScript™ Reverse Transcription System (Promega, Wisconsin, USA) was used to synthesize cDNA from the RNA. The cDNA was synthesized by performing annealing using 1 µg of RNA, 0.5 µg of an oligo dt primer, 0.5 µg of a random primer and RT-PCR pre-mixture at 25° C. for 5 minutes, extension at 42° C. for 60 minutes, and inactivation at 70° C. for 15 minutes.

(3) cDNA Synthesis and PCR

PCR was performed using Maxime™ PCR PreMix (i-StarTaq) (Intron Biotechnology, Korea). Real-time PCR was performed using SsoAdvanced™ Universal SYBR® Green Supermix (Bio-Rad, USA). 100 ng of cDNA, 2 µM (pmol/µl) primers, 10 µl of 2X SsoAdvanced™ Universal SYBR® Green Supermix and DW were added to the PCR plate well. Then, the temperature was cyclically adjusted to 95° C. for 3 minutes, 95° C. for 10 seconds and 58° C. for 40 seconds for a total of 40 cycles. A PCR reaction was performed using a CFX96 Touch™ Real-Time PCR Detection System (Bio-Rad, California, USA), and fluorescence intensity was measured at the end of each cycle. The primer sequences used for PCR analysis to detect Nrf2 expression are shown in Table 4 below.

TABLE 4

| Gene | Sequence |
|---|---|
| Nrf2 | Forward: 5'-ATTCCTTCAGCAGCATCC-3' (SEQ ID NO: 101) |
| | Reverse: 5'-GTGTTGACTGTGGCATCT-3' (SEQ ID NO: 102) |

TABLE 4-continued

| Gene | Sequence |
|------|----------|
| 18S  | Forward: 5'-GAGCCTGAGAAACGGCTAC-3' (SEQ ID NO: 103)<br>Reverse: 5'-CCCATTATTCCTAGCTGCG-3' (SEQ ID NO: 104) |

3. Conclusion

Figure 5A:
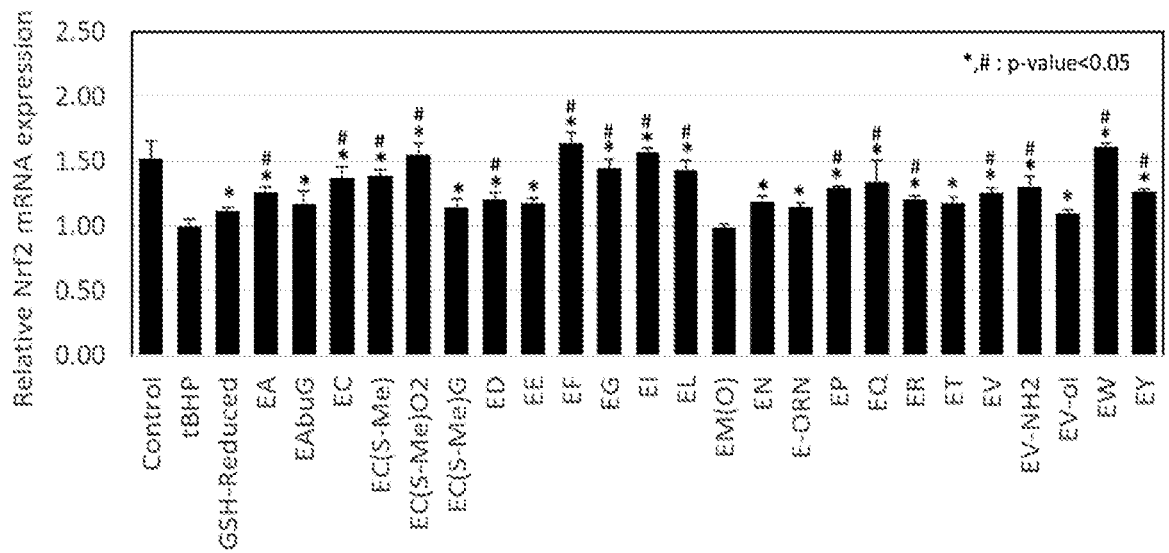
FIGS. 5A to 5C are graphs showing the result of real-time PCR for detecting expression levels of Nrf2 mRNA in 100 types of peptides identified from yeast hydrolysates.
Figure 5B:
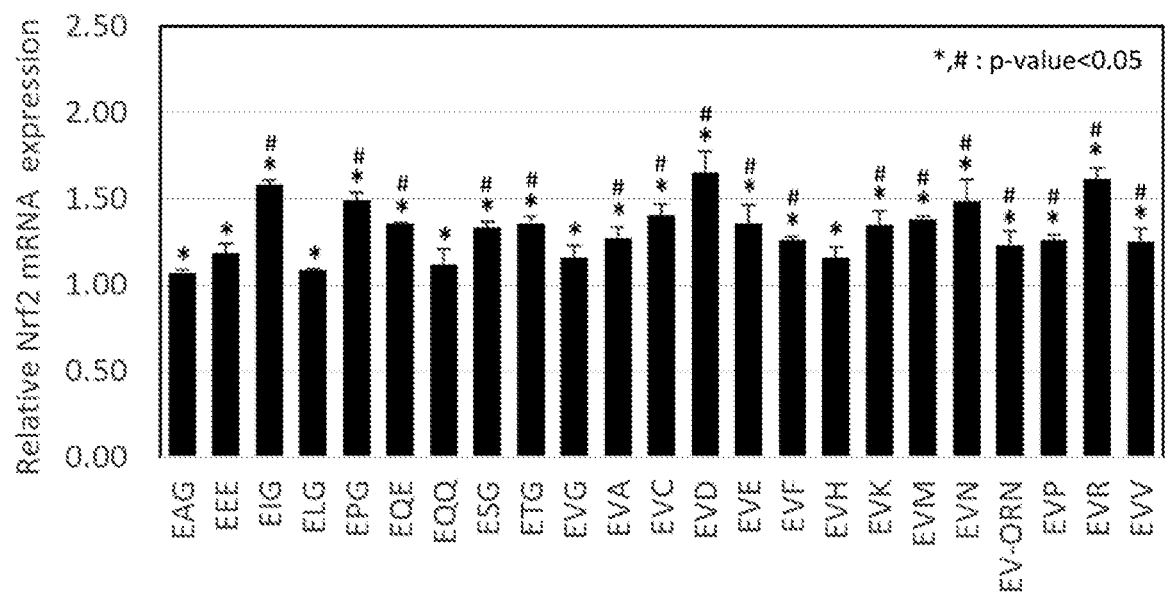
Figure 5C:
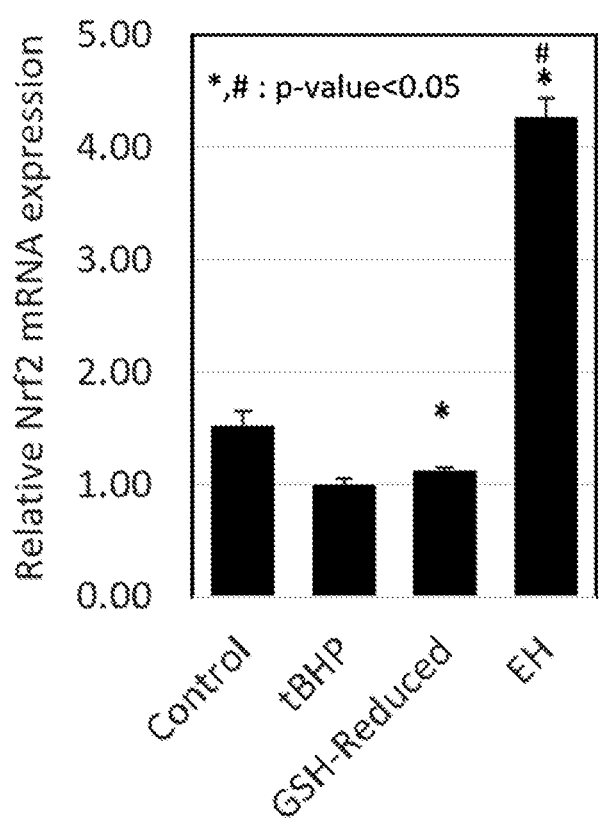

FIGS. 5A to 5C are graphs showing the result of real-time PCR for detecting expression levels of Nrf2 mRNA in 100 types of peptides identified from yeast hydrolysates. FIGS. 5A to 5C show control, treatment only with tBHP (direct-acting oxidative stress-inducing agent) as a negative control, treatment with tBHP and then GSH peptide as a positive control and the names of 100 types of peptides (see Tables 5 and 6) corresponding thereto.

A total of 100 types of peptides obtained in Experimental Example 4 were identified. The amount of Nrf2 mRNA expression was compared between the peptides. As a result, a total of 48 peptides having an increased amount of Nrf2 mRNA were selected, the Nrf2 mRNA expression levels thereof were quantitatively measured, and the results are shown in FIGS. 5A to 5C, and the chemical formulas and structural formulas of 48 types of selected peptides and the remaining non-selected peptides are shown in Tables 5 and 6 below. Table 5 shows the sequences of 48 types of selected peptides. Table 6 shows the sequence of non-selected peptides.

TABLE 5

| SEQ ID NO: | Name | Amino acid sequence | Chemical structure | Molecular weight ([M + H]$^+$(m/z)) |
|---|---|---|---|---|
| Positive control | ECG-reduced | GSH-reduced | C10H17N3O6S | 308.0916 |
| 1 | EA | γ-GLU-ALA | C8H14N2O5 | 219.0981 |
| 2 | EC | γ-GLU-CYS | C8H14N2O5S | 251.0702 |
| 3 | EC(S-Me) | γ-GLU-CYS(S-Me) | C9H16N2O5S | 265.0858 |
| 4 | EC(S-Me)(O2) | γ-GLU-CYS(S-Me)(O2) | C9H16N2O7S | 297.0756 |
| 5 | ED | γ-GLU-ASP | C9H14N2O7 | 263.0879 |
| 6 | EE | γ-GLU-GLU | C10H16N2O7 | 277.1036 |
| 7 | EF | γ-GLU-PHE | C14H18N2O5 | 295.1294 |
| 8 | EG | γ-GLU-GLY | C7H12N2O5 | 205.0824 |
| 9 | EH | γ-GLU-HIS | C11H16N4O5 | 285.1199 |
| 10 | EI | γ-GLU-ILE | C11H20N2O5 | 261.1450 |
| 11 | EL | γ-GLU-LEU | C11H20N2O5 | 261.1450 |
| 12 | EM(O) | γ-GLU-MET(O) | C10H18N2O6S | 295.0964 |
| 13 | EN | γ-GLU-ASN | C9H15N3O6 | 262.1039 |
| 14 | E-ORN | γ-GLU-ORN | C10H19N3O5 | 262.1403 |
| 15 | EP | γ-GLU-PRO | C10H16N2O5 | 245.1137 |
| 16 | EQ | γ-GLU-GLN | C10H17N3O6 | 276.1196 |
| 17 | ER | γ-GLU-ARG | C11H21N5O5 | 304.1621 |
| 18 | ET | γ-GLU-THR | C9H16N2O6 | 249.1087 |
| 19 | EV | γ-GLU-VAL | C10H18N2O5 | 247.1294 |
| 20 | EV-NH2 | γ-GLU-VAL-NH2 | C10H19N3O4 | 246.1454 |
| 21 | EW | γ-GLU-TRP | C16H19N3O5 | 334.1403 |
| 22 | EY | γ-GLU-TYR | C14H18N2O6 | 311.1243 |
| 23 | EV-ol | γ-GLU-VAL-ol | C10H18N2O3 | 215.1396 |
| 24 | EQE | γ-GLU-GLN-GLU | C15H24N4O9 | 405.1622 |
| 25 | EAG | γ-GLU-ALA-GLY | C10H17N3O6 | 276.1196 |
| 26 | EEE | γ-GLU-GLU-GLU | C15H23N3O10 | 406.1462 |
| 27 | EIG | γ-GLU-ILE-GLY | C13H23N3O6 | 318.1665 |
| 28 | EPG | γ-GLU-PRO-GLY | C12H19N3O6 | 302.1352 |
| 29 | EQQ | γ-GLU-GLN-GLN | C15H25N5O8 | 404.1781 |
| 30 | ESG | γ-GLU-SER-GLY | C10H17N3O7 | 292.1145 |
| 31 | ETG | γ-GLU-THR-GLY | C11H19N3O7 | 306.1301 |
| 32 | EVG | γ-GLU-VAL-GLY | C12H21N3O6 | 304.1509 |
| 33 | EVA | γ-GLU-VAL-ALA | C13H23N3O6 | 318.1665 |
| 34 | EVC | γ-GLU-VAL-CYS | C13H23N3O6S | 350.1386 |
| 35 | EVD | γ-GLU-VAL-ASP | C14H23N3O8 | 362.1563 |
| 36 | EVE | γ-GLU-VAL-GLU | C15H25N3O8 | 376.1720 |
| 37 | EVF | γ-GLU-VAL-PHE | C19H27N3O6 | 394.1978 |
| 38 | EVH | γ-GLU-VAL-HIS | C16H25N5O6 | 384.1883 |
| 39 | EVK | γ-GLU-VAL-LYS | C16H30N4O6 | 375.2244 |
| 40 | EVM | γ-GLU-VAL-MET | C15H27N3O6S | 378.1699 |
| 41 | EVN | γ-GLU-VAL-ASN | C14H24N4O7 | 361.1723 |
| 42 | EV-ORN | γ-GLU-VAL-ORN | C15H28N4O6 | 361.2087 |
| 43 | EVP | γ-GLU-VAL-PRO | C15H25N3O6 | 344.1822 |
| 44 | EVR | γ-GLU-VAL-ARG | C16H30N6O6 | 403.2305 |
| 45 | EVV | γ-GLU-VAL-VAL | C15H27N3O6 | 346.1978 |
| 46 | EC(S-Me)G | γ-GLU-CYS(S-Me)-GLY | C11H19N3O6S | 322.1073 |
| 47 | EAbuG | γ-GLU-Abu-GLY | C11H19N3O6 | 290.1352 |
| 48 | ELG | γ-GLU-LEU-GLY | C13H23N3O6 | 318.1665 |

TABLE 6

| SEQ ID NO: | Name | Amino acid sequence | Chemical structure | Molecular weight ([M + H]$^+$(m/z)) |
|---|---|---|---|---|
| 49 | E-Abu | GLU-Abu | C9H16N2O5 | 233.1059 |
| 50 | α-EH | α-GLU-HIS | C11H16N4O5 | 285.1199 |
| 51 | β-EH | β-GLU-HIS | C11H16N4O5 | 285.1199 |
| 52 | EK | γ-GLU-LYS | C11H21N3O5 | 276.1559 |
| 53 | EM | γ-GLU-MET | C10H18N2O5S | 279.1015 |
| 54 | E-Nle | γ-GLU-Nle | C11H20N2O5 | 261.1372 |
| 55 | E-Nva | γ-GLU-Nva | C10H18N2O5 | 247.1294 |
| 56 | ES | γ-GLU-SER | C8H14N2O6 | 235.0930 |
| 57 | EtL | γ-GLU-tLEU | C11H20N2O6 | 261.1450 |
| 58 | E-Abu-L | γ-GLU-Abu-LEU | C15H27N3O6 | 346.1900 |
| 59 | E-Abu-P | γ-GLU-Abu-PRO | C14H23N3O6 | 330.3489 |
| 60 | EAF | γ-GLU-ALA-PHE | C17H23N3O6 | 366.1665 |
| 61 | EAI | γ-GLU-ALA-ILE | C14H25N3O6 | 332.1822 |
| 62 | EAL | γ-GLU-ALA-LEU | C14H25N3O6 | 332.1822 |
| 63 | EAP | γ-GLU-ALA-PRO | C13H21N3O6 | 316.1509 |
| 64 | EAW | γ-GLU-ALA-TRP | C19H24N4O6 | 405.1774 |
| 65 | EAY | γ-GLU-ALA-TYR | C17H23N3O6 | 382.1614 |
| 66 | EC-βA | γ-GLU-CYS-βALA | C11H19N3O6 | 322.1073 |
| 67 | EDF | γ-GLU-ASP-PHE | C18H23N3O8 | 410.1563 |
| 68 | EDM | γ-GLU-ASP-MET | C14H23N3O8S | 394.1284 |
| 69 | EEF | γ-GLU-GLU-PHE | C19H25N3O8 | 424.1720 |
| 70 | EEQ | γ-GLU-GLU-GLN | C15H24N4O9 | 405.1622 |
| 71 | EFA | γ-GLU-PHE-ALA | C17H23N3O6 | 366.1665 |
| 72 | EFV | γ-GLU-PHE-VAL | C19H27N3O6 | 394.1978 |
| 73 | EGA | γ-GLU-GLY-ALA | C10H17N3O6 | 276.1196 |
| 74 | EGG | γ-GLU-GLY-GLY | C9H15N3O6 | 262.0961 |
| 75 | EGW | γ-GLU-GLY-TRP | C18H22N4O6 | 391.1618 |
| 76 | EGY | γ-GLU-GLY-TYR | C16H21N3O7 | 368.1458 |
| 77 | EIA | γ-GLU-ILE-ALA | C14H25N3O6 | 332.1822 |
| 78 | EIF | γ-GLU-ILE-PHE | C20H29N3O6 | 408.2135 |
| 79 | EIS | γ-GLU-ILE-SER | C14H25N3O7 | 348.1771 |
| 80 | EIT | γ-GLU-ILE-THR | C15H27N3O7 | 362.1927 |
| 81 | EIV | γ-GLU-ILE-VAL | C16H29N3O6 | 360.2135 |
| 82 | ELN | γ-GLU-LEU-ASN | C15H26N4O7 | 375.1880 |
| 83 | ELS | γ-GLU-LEU-SER | C14H25N3O7 | 348.1771 |
| 84 | ELV | γ-GLU-LEU-VAL | C16H29N3O6 | 360.2135 |
| 85 | ENvaG | γ-GLU-Nva-GLY | C12H21N3O6 | 304.3116 |
| 86 | EPD | γ-GLU-PRO-ASP | C14H21N3O8 | 360.1407 |
| 87 | ERY | γ-GLU-ARG-TYR | C20H3ON6O7 | 467.2254 |
| 88 | ESY | γ-GLU-SER-TYR | C17H23N3O8 | 398.1563 |
| 89 | ETC | γ-GLU-THR-CYS | C12H21N3O7S | 352.1178 |
| 90 | ETD | γ-GLU-THR-ASP | C13H21N3O9 | 364.1356 |
| 91 | ETH | γ-GLU-THR-HIS | C15H23N5O7 | 386.1676 |
| 92 | ETQ | γ-GLU-THR-GLN | C14H24N4O8 | 377.1672 |
| 93 | ETR | γ-GLU-THR-ARG | C15H28N6O7 | 405.2098 |
| 94 | ETS | γ-GLU-THE-SER | C12H21N3O8 | 336.1407 |
| 95 | EVQ | γ-GLU-VAL-GLN | C15H26N4O7 | 375.1880 |
| 96 | EVS | γ-GLU-VAL-SER | C13H23N3O7 | 334.1614 |
| 97 | EVT | γ-GLU-VAL-THR | C14H25N3O7 | 348.1771 |
| 98 | EWA | γ-GLU-TRP-ALA | C19H24N4O6 | 405.1774 |
| 99 | EWC | γ-GLU-TRP-CYS | C19H24N4O6S | 437.1495 |
| 100 | EWE | γ-GLU-TRP-GLU | C21H26N4O8 | 463.1829 |

In Table 6, α-GLU means glutamic acid, β-GLU means β-glutamic acid, Nle means norleucine, Nva means norvaline, tL or tLEU means tert-leucine, and βA or KALA means β-alanine. In addition, the sequence represented by γ-GLU means that amino acid residues are sequentially bonded to the gamma chain of L-glutamic acid.

That is, a total of 100 types of peptides were identified from yeast hydrolysates, but a total of 48 types of peptides with antioxidant activity promoting Nrf2 mRNA expression were detected.

The growth of normal cells, which are treated with tBHP as an oxidizing agent, is inhibited by oxidative stress. When the tBHP-treated cells are treated with a peptide having an antioxidant effect, oxidation and growth inhibition of the cells caused by tBHP are reduced.

As can be seen from FIGS. 5A to 5C, 48 types of peptides (γ-GLU-ALA, γ-GLU-CYS, γ-GLU-CYS(S-Me), γ-GLU-CYS(S-Me) (02), γ-GLU-ASP, γ-GLU-GLU, γ-GLU-PHE, γ-GLU-GLY, γ-GLU-HIS, γ-GLU-ILE, γ-GLU-LEU, γ-GLU-MET(O), γ-GLU-ASN, γ-GLU-ORN, γ-GLU-PRO, γ-GLU-GLN, γ-GLU-ARG, γ-GLU-THR, γ-GLU-VAL, γ-GLU-VAL-NH2, γ-GLU-TRP, γ-GLU-TYR, γ-GLU-VAL-ol, γ-GLU-GLN-GLU, γ-GLU-ALA-GLY, γ-GLU-GLU-GLU, γ-GLU-ILE-GLY, γ-GLU-PRO-GLY, γ-GLU-GLN-GLN, γ-GLU-SER-GLY, γ-GLU-THR-GLY, γ-GLU-VAL-GLY, γ-GLU-VAL-ALA, γ-GLU-VAL-CYS, γ-GLU-VAL-ASP, γ-GLU-VAL-GLU, γ-GLU-VAL-PHE, γ-GLU-VAL-HIS, γ-GLU-VAL-LYS, γ-GLU-VAL-MET, γ-GLU-VAL-ASN, γ-GLU-VAL-ORN, γ-GLU-VAL-PRO, γ-GLU-VAL-ARG, γ-GLU-VAL-VAL, γ-GLU-CYS(S-Me)-GLY, γ-GLU-Abu-GLY and γ-GLU-LEU-GLY) function to improve the expression of Nrf2 mRNA.

In addition, among the 48 types of peptides, dipeptides having the effect of improving Nrf2 mRNA expression so as to be comparable or superior to the positive control GSH were identified to be γ-GLU-ALA, γ-GLU-CYS, γ-GLU-CYS(S-Me), γ-GLU-CYS(S-Me) (02), γ-GLU-ASP, γ-GLU-GLU, γ-GLU-PHE, γ-GLU-GLY, γ-GLU-HIS, γ-GLU-ILE, γ-GLU-LEU, γ-GLU-ASN, γ-GLU-ORN, γ-GLU-PRO, γ-GLU-GLN, γ-GLU-ARG, γ-GLU-THR, γ-GLU-VAL, γ-GLU-VAL-NH2, γ-GLU-TRP, γ-GLU-TYR and γ-GLU-VAL-ol, and exhibited an effect comparable or superior to that of GSH in spite of having a shorter sequence than GSH.

In addition, among the 48 peptides, tripeptides having a remarkably excellent effect of increasing Nrf2 mRNA expression compared to the positive control GSH were identified to be γ-GLU-GLN-GLU, γ-GLU-ILE-GLY, γ-GLU-PRO-GLY, γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN and γ-GLU-VAL-ARG. More preferably, it can be seen that γ-GLU-CYS(S-Me) (02) or γ-GLU-HIS increases the expression level of Nrf2 mRNA at the same concentration by more than four times compared to GSH, the positive control (the expression of Nrf2 mRNA was recovered to the normal level). In particular, α-GLU-HIS and β-GLU-HIS had no effect compared to γ-GLU-HIS.

Experimental Example 6. Analysis of SOD2 mRNA Expression Level of 100 Types of Peptides The expression of SOD2 mRNA as another antioxidant factor was determined. The cell line culture, RNA extraction, cDNA synthesis and PCR experiments were performed in the same manner as in Experimental Example 5 above. A detailed description thereof is given below.

1. Analysis of Antioxidant Activity (SOD2 mRNA Expression Level) of 100 Types of Peptides in Experimental Example 5

(1) Cell Culture and Treatment with 100 Types of Peptides

An HEK293 cell (kidney cell) line was seeded at a density of 6.6×10$^5$/well in DMEM (Dulbecco's Modified Eagle's Medium) medium on a 6-well plate and cultured at 37° C. and 5% CO$_2$ for 24 hours. The next day, the medium was exchanged with serum and amino-acid-free media, and then the cells were further cultured for 20 hours or longer. The cells were treated with Tert-BHP (300 μM) and 500 μM 100 types of peptides, and then cultured for 18 hours.

(2) RNA Extraction

RNA was extracted from the cells treated with 100 types of peptides in (1) using TRIzol (Thermo Fisher Scientific). A GoScript™ Reverse Transcription System (Promega, Wisconsin, USA) was used to synthesize cDNA from the RNA. The cDNA was synthesized by performing annealing with 1 μg RNA, 0.5 μg of an oligo dt primer, 0.5 μg of a random primer, and RT-PCR pre-mixture at 25° C. for 5 minutes, extension at 42° C. for 60 minutes, and inactivation at 70° C. for 15 minutes.

(3) cDNA Synthesis and PCR

PCR was performed using Maxime™ PCR PreMix (i-StarTaq) (Intron Biotechnology, Korea). Real-time PCR was performed using SsoAdvanced™ Universal SYBR® Green Supermix (Bio-Rad, USA). 100 ng of cDNA, 2 μM (pmol/μl) primers, 10 μl of 2X SsoAdvanced™ Universal SYBR® Green Supermix and DW were added to the PCR plate well. Then, the temperature was cyclically adjusted to 95° C. for 3 minutes, 95° C. for 10 seconds and 58° C. for 40 seconds for a total of 40 cycles. A PCR reaction was performed using the CFX96 Touch™ Real-Time PCR Detection System (Bio-Rad, California, USA), and fluorescence intensity was measured at the end of each cycle. The primer sequences used for PCR analysis to detect SOD2 mRNA expression are shown in Table 7 below.

TABLE 7

| Gene | Sequence |
|------|----------|
| SOD2 | Forward: 5'-GCACATTAACGCGCAGATCA -3' (SEQ ID NO: 105)<br>Reverse: 5'-AGCCTCCAGCAACTCTCCTT-3' (SEQ ID NO: 106) |
| GAPDH | Forward: 5'-GTATGACAACAGCCTCAAGAT-3' (SEQ ID NO: 107)<br>Reverse: 5'-AGTCCTTCCACGATACCAAA-3' (SEQ ID NO: 108) |

2. Conclusion

Figure 6:
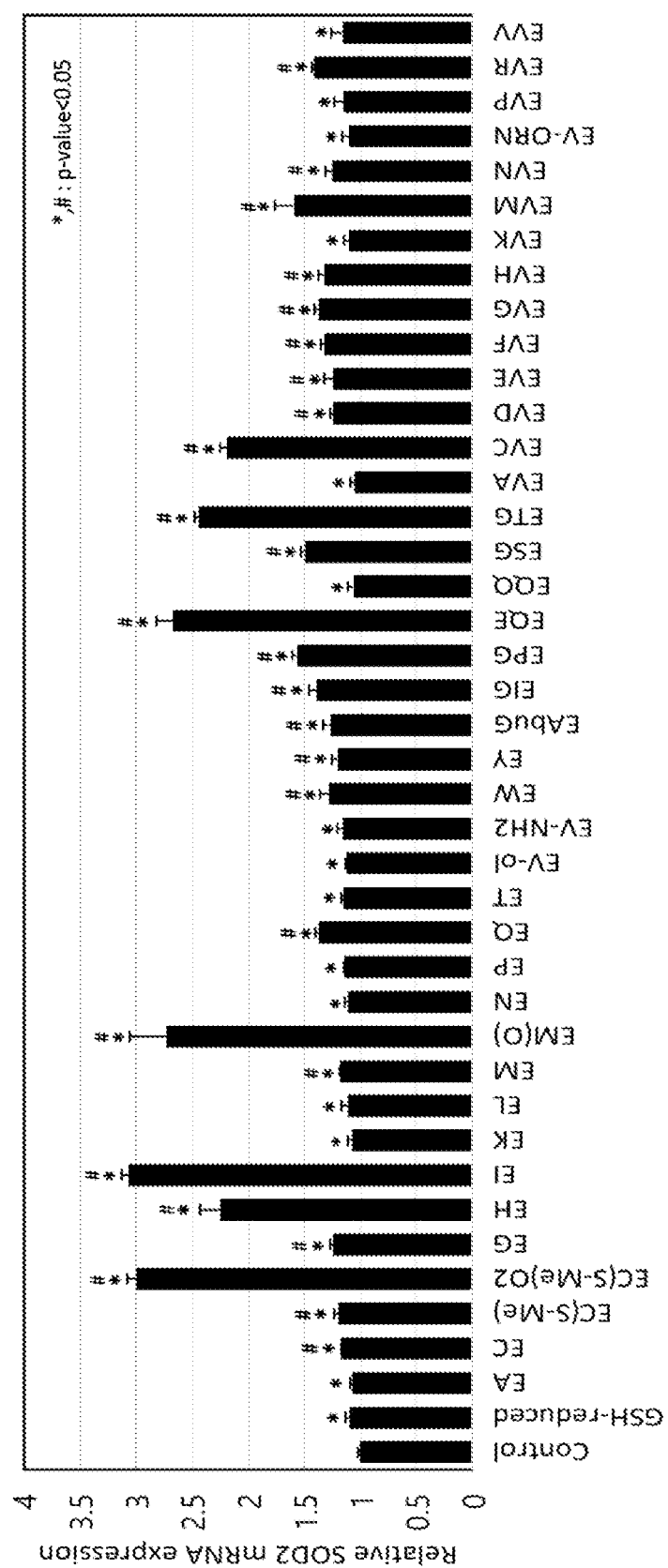
FIG. 6 is a graph showing the result of real-time PCR for detecting expression levels of SOD2 mRNA in 100 types of peptides identified from yeast hydrolysates.

FIG. 6 is a graph showing the result of real-time PCR for detecting expression levels of SOD2 mRNA in 100 types of peptides identified from yeast hydrolysates. FIG. 6 shows a control and treatment with tBHP and then GSH peptide as a positive control, and the names of 48 types of peptides in Table 5.

As shown in FIG. 6, the relative SOD2 mRNA expression induced by oxidative stress was measured, and the antioxidant efficacy was compared between respective peptides. RT-PCR was performed on a total of 100 peptides obtained from yeast hydrolysates. The result identified that the following 39 types of peptides have increased SOD2 mRNA expression: γ-GLU-CYS(S-Me) (O2), γ-GLU-HIS, γ-GLU-ILE-GLY, γ-GLU-PRO-GLY, γ-GLU-GLN-GLU, γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN, γ-GLU-VAL-ARG, γ-GLU-ALA, γ-GLU-CYS, γ-GLU-CYS(S-Me), γ-GLU-GLY, γ-GLU-ILE, γ-GLU-LYS, γ-GLU-LEU, γ-GLU-MET, γ-GLU-MET(O), γ-GLU-ASN, γ-GLU-PRO, γ-GLU-GLN, γ-GLU-THR, γ-GLU-VAL-NH2, γ-GLU-VAL-ol, γ-GLU-TRP, γ-GLU-TYR, γ-GLU-Abu-GLY, γ-GLU-GLN-GLN, γ-GLU-VAL-ALA, γ-GLU-VAL-GLY, γ-GLU-VAL-HIS, γ-GLU-VAL-LYS, γ-GLU-VAL-ORN, γ-GLU-VAL-PRO, and γ-GLU-VAL-VAL. The peptides other than the 39 types of peptides had almost no effect of improving SOD2 mRNA expression.

As a result of quantitatively analyzing the SOD2 mRNA expression in the 39 kinds of peptides, dipeptides having an SOD2 mRNA expression level comparable or superior to the positive control, GSH, were identified to be γ-GLU-ALA, γ-GLU-CYS, γ-GLU-CYS(S-Me), γ-GLU-CYS(S-Me) (O2), γ-GLU-GLY, γ-GLU-HIS, γ-GLU-ILE, γ-GLU-LYS, γ-GLU-LEU, γ-GLU-MET, γ-GLU-MET(O), γ-GLU-ASN, γ-GLU-PRO, γ-GLU-GLN, γ-GLU-THR, γ-GLU-VAL-NH2, γ-GLU-TRP, γ-GLU-TYR and γ-GLU-VAL-ol, which exhibited a comparable or superior effect to GSH in spite of having a shorter sequence than GSH.

In addition, tripeptides having remarkably excellent SOD2 mRNA expression compared to the positive control GSH were identified to be γ-GLU-GLN-GLU, γ-GLU-Abu-GLY, γ-GLU-ILE-GLY, γ-GLU-PRO-GLY, γ-GLU-SER-GLY, γ-GLU-THR-GLY, γ-GLU-VAL-CYS, γ-GLU-VAL-ASP, γ-GLU-VAL-GLU, γ-GLU-VAL-GLY, γ-GLU-VAL-HIS, γ-GLU-VAL-PHE, γ-GLU-VAL-MET, γ-GLU-VAL-ASN and γ-GLU-VAL-ARG.

Preferably, γ-GLU-CYS(S-Me) (O2), γ-GLU-HIS, γ-GLU-ILE, γ-GLU-MET(O), γ-GLU-GLN-GLU, γ-GLU-THR-GLY, and γ-GLU-VAL-CYS exhibited a remarkably higher effect of increasing SOD2 mRNA expression about 2 to 3 times higher than the normal level (remarkably higher SOD2 mRNA expression than the normal level (control)).

In conclusion, the test results proved that yeast (Saccharomyces cerevisiae) cells were heated to 60° C. and treated with Alcalase for 4 hours to conduct cell lysis, Flavourzyme was added thereto to conduct enzymatic lysis for 10 hours, and Alcalase and Flavourzyme were added thereto to conduct enzymatic lysis for 24 hours, and a supernatant was collected to prepare a yeast hydrolyzate. A fraction having a molecular weight of 1 kDa or less was primarily separated from the yeast hydrolyzate thus prepared through an ultrafiltration membrane, and a fraction having a molecular weight ([M+H]$^+$ (m/z)) of 219.0981 to 406.1462 was secondarily separated therefrom through HPLC. Then, a total of 100 types of peptides were identified therefrom.

The result of analysis of the antioxidant activity (Nrf2, SOD2 mRNA) on the 100 types of peptides showed that a total of 48 kinds of peptides (γ-GLU-ALA, γ-GLU-CYS, γ-GLU-CYS(S-Me), γ-GLU-CYS(S-Me) (O2), γ-GLU-ASP, γ-GLU-GLU, γ-GLU-PHE, γ-GLU-GLY, γ-GLU-HIS, γ-GLU-ILE, γ-GLU-LEU, γ-GLU-MET(O), γ-GLU-ASN, γ-GLU-ORN, γ-GLU-PRO, γ-GLU-GLN, γ-GLU-ARG, γ-GLU-THR, γ-GLU-VAL, γ-GLU-VAL-NH2, γ-GLU-TRP, γ-GLU-TYR, γ-GLU-VAL-ol, γ-GLU-GLN-GLU, γ-GLU-ALA-GLY, γ-GLU-GLU-GLU, γ-GLU-ILE-GLY, γ-GLU-PRO-GLY, γ-GLU-GLN-GLN, γ-GLU-SER-GLY, γ-GLU-THR-GLY, γ-GLU-VAL-GLY, γ-GLU-VAL-ALA, γ-GLU-VAL-CYS, γ-GLU-VAL-ASP, γ-GLU-VAL-GLU, γ-GLU-VAL-PHE, γ-GLU-VAL-HIS, γ-GLU-VAL-LYS, γ-GLU-VAL-MET, γ-GLU-VAL-ASN, γ-GLU-VAL-ORN, γ-GLU-VAL-PRO, γ-GLU-VAL-ARG, γ-GLU-VAL-VAL, γ-GLU-CYS(S-Me)-GLY, γ-GLU-Abu-GLY and γ-GLU-LEU-GLY) have antioxidant activity.

Among the dipeptides having a shorter sequence length than the positive control GSH, γ-GLU-ALA, γ-GLU-CYS, γ-GLU-CYS(S-Me), γ-GLU-CYS(S-Me) (O2), γ-GLU-GLY, γ-GLU-HIS, γ-GLU-ILE, γ-GLU-LEU, γ-GLU-ASN, γ-GLU-PRO, γ-GLU-GLN, γ-GLU-THR, γ-GLU-VAL-NH2, γ-GLU-TRP, γ-GLU-TYR and γ-GLU-VAL-ol were found to have remarkably excellent activity of promoting Nrf2 and SOD2 expression comparable or superior to GSH. Among them, dipeptides having statistically significant activity of promoting Nrf2 and SOD2 expression compared to GSH are identified to be γ-GLU-CYS, γ-GLU-CYS(S-Me), γ-GLU-CYS(S-Me) (O2), γ-GLU-GLY, γ-GLU-HIS, γ-GLU-ILE, γ-GLU-LEU, γ-GLU-GLN, γ-GLU-TRP and γ-GLU-TYR.

In addition, it was found that, among the tripeptides having the same sequence length as the positive control GSH, γ-GLU-GLN-GLU, γ-GLU-ILE-GLY, γ-GLU-PRO- GLY, γ-GLU-SER-GLY, γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN and γ-GLU-VAL-ARG have statistically significant activity of promoting Nrf2 and SOD2 expression compared to GSH.

That is, a total of 21 types of peptides having better effects of promoting Nrf2 expression and SOD2 expression than GSH, which is conventionally and widely known to have antioxidant effects, were identified to be γ-GLU-CYS(S-Me) (O2), γ-GLU-HIS, γ-GLU-CYS, γ-GLU-CYS(S-Me), γ-GLU-GLY, γ-GLU-ILE, γ-GLU-GLN, γ-GLU-TRP, γ-GLU-TYR, γ-GLU-GLN-GLU, γ-GLU-ILE-GLY, γ-GLU-PRO-GLY, γ-GLU-SER-GLY, γ-GLU-THR-GLY, γ-GLU-VAL-CYS, γ-GLU-VAL-ASP, γ-GLU-VAL-GLU, γ-GLU-VAL-PHE, γ-GLU-VAL-MET, γ-GLU-VAL-ASN and γ-GLU-VAL-ARG.

It was found that among them, 6 types of peptides (γ-GLU-CYS(S-Me) (O2), γ-GLU-HIS, γ-GLU-ILE, γ-GLU-GLN-GLU, γ-GLU-THR-GLY, and γ-GLU-VAL-CYS) have antioxidant effects (reducing power, DPPH-scavenging ability and Nrf2 mRNA activity comparable or superior to GSH), and have an effect of promoting SOD2 mRNA expression 2 to 3 times higher than that of the positive control, GSH, and γ-GLU-HIS exhibits an effect of promoting Nrf2 and SOD2 mRNA expression 2 to 8 times higher than that of GSH.

SEQUENCE LISTING

```
<160> NUMBER OF SEQ ID NOS: 108

<210> SEQ ID NO 1
<211> LENGTH: 2
<212> TYPE: PRT
<213> ORGANISM: Artificial Sequence
<220> FEATURE:
<223> OTHER INFORMATION: The peptide is formed by condensation of the
      gamma-carboxy group of L-glutamic acid with the amino group of
      L-alanine.

<400> SEQUENCE: 1

Glu Ala
1

<210> SEQ ID NO 2
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-cysteine.

<400> SEQUENCE: 2

Glu Cys
1

<210> SEQ ID NO 3
<211> LENGTH: 2
<212> TYPE: PRT
<213> ORGANISM: Artificial Sequence
<220> FEATURE:
<223> OTHER INFORMATION: In the peptide, Cys is Cys(s-Me), which is
      characterized in that the hydrogen of the thiol group is
      substituted with a methyl group. The peptide is a formed by
      condensation of the gamma-carboxy group of L-glutamic acid with
      the amino group of
<220> FEATURE:
<221> NAME/KEY: MISC_FEATURE
<222> LOCATION: (2)..(2)
<223> OTHER INFORMATION: cysteine in which hydrogen of the thiol group
      is substituted with a methyl group

<400> SEQUENCE: 3

Glu Cys
1

<210> SEQ ID NO 4
<211> LENGTH: 2
<212> TYPE: PRT
<213> ORGANISM: Artificial Sequence
<220> FEATURE:
<223> OTHER INFORMATION: In the peptide, Cys is Cys(Me)(O2), which is
      characterized in that the hydrogen of the thiol group is
```

```
        substituted with a methyl group and has a sulfoxide structure.
        Cys(Me)(O2) can be referred to as S-(methyl)-cysteine sulfoxide.
        The peptide is a formed by
<220> FEATURE:
<221> NAME/KEY: MISC_FEATURE
<222> LOCATION: (2)..(2)
<223> OTHER INFORMATION: cysteine in which hydrogen of the thiol group
        is substituted with a methyl group and which has a sulfoxide
        structure

<400> SEQUENCE: 4

Glu Cys
1

<210> SEQ ID NO 5
<211> LENGTH: 2
<212> TYPE: PRT
<213> ORGANISM: Artificial Sequence
<220> FEATURE:
<223> OTHER INFORMATION: The peptide is a formed by condensation of the
        gamma-carboxy group of L-glutamic acid with the amino group of
        L-aspartic acid.

<400> SEQUENCE: 5

Glu Asp
1

<210> SEQ ID NO 6
<211> LENGTH: 2
<212> TYPE: PRT
<213> ORGANISM: Artificial Sequence
<220> FEATURE:
<223> OTHER INFORMATION: The peptide is a formed by condensation of the
        gamma-carboxy group of L-glutamic acid with the amino group of
        L-glutamic acid.

<400> SEQUENCE: 6

Glu Glu
1

<210> SEQ ID NO 7
<211> LENGTH: 2
<212> TYPE: PRT
<213> ORGANISM: Artificial Sequence
<220> FEATURE:
<223> OTHER INFORMATION: The peptide is a formed by condensation of the
        gamma-carboxy group of L-glutamic acid with the amino group of
        L-phenylalanine.

<400> SEQUENCE: 7

Glu Phe
1

<210> SEQ ID NO 8
<211> LENGTH: 2
<212> TYPE: PRT
<213> ORGANISM: Artificial Sequence
<220> FEATURE:
<223> OTHER INFORMATION: The peptide is a formed by condensation of the
        gamma-carboxy group of L-glutamic acid with the amino group of
        L-glycine.

<400> SEQUENCE: 8

Glu Gly
1

<210> SEQ ID NO 9
<211> LENGTH: 2
<212> TYPE: PRT
```

```
<213> ORGANISM: Artificial Sequence
<220> FEATURE:
<223> OTHER INFORMATION: The peptide is a formed by condensation of the
      gamma-carboxy group of L-glutamic acid with the amino group of
      L-histidine.

<400> SEQUENCE: 9

Glu His
1

<210> SEQ ID NO 10
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-isoleucine.

<400> SEQUENCE: 10

Glu Ile
1

<210> SEQ ID NO 11
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-leucine.

<400> SEQUENCE: 11

Glu Leu
1

<210> SEQ ID NO 12
<211> LENGTH: 2
<212> TYPE: PRT
<213> ORGANISM: Artificial Sequence
<220> FEATURE:
<223> OTHER INFORMATION: In the peptide, Met is methionune
      sulfoxide(Met(O)). The peptide is a formed by condensation of the
      gamma-carboxy group of L-glutamic acid with the amino group of
      Met(O).
<220> FEATURE:
<221> NAME/KEY: MISC_FEATURE
<222> LOCATION: (2)..(2)
<223> OTHER INFORMATION: methionine sulfoxide

<400> SEQUENCE: 12

Glu Met
1

<210> SEQ ID NO 13
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-asparagine.

<400> SEQUENCE: 13

Glu Asn
1

<210> SEQ ID NO 14
<211> LENGTH: 2
```

```
<212> TYPE: PRT
<213> ORGANISM: Artificial Sequence
<220> FEATURE:
<223> OTHER INFORMATION: In the peptide, Xaa is ornithine(Orn). The
      peptide is a formed by condensation of the gamma-carboxy group of
      L-glutamic acid with the amino group of ornithine
<220> FEATURE:
<221> NAME/KEY: MOD_RES
<222> LOCATION: (2)..(2)
<223> OTHER INFORMATION: Orn

<400> SEQUENCE: 14

Glu Xaa
1

<210> SEQ ID NO 15
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-proline.

<400> SEQUENCE: 15

Glu Pro
1

<210> SEQ ID NO 16
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-glutamine.

<400> SEQUENCE: 16

Glu Gln
1

<210> SEQ ID NO 17
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-arginine.

<400> SEQUENCE: 17

Glu Arg
1

<210> SEQ ID NO 18
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-threonine.

<400> SEQUENCE: 18

Glu Thr
1

<210> SEQ ID NO 19
<211> LENGTH: 2
```

```
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-valine.

<400> SEQUENCE: 19

Glu Val
1

<210> SEQ ID NO 20
<211> LENGTH: 2
<212> TYPE: PRT
<213> ORGANISM: Artificial Sequence
<220> FEATURE:
<223> OTHER INFORMATION: In the peptide, Val is L-valine amide(Val-NH2).
      The peptide is a formed by condensation of the gamma-carboxy group
      of L-glutamic acid with the amino group of L-valine amide.
<220> FEATURE:
<221> NAME/KEY: MISC_FEATURE
<222> LOCATION: (2)..(2)
<223> OTHER INFORMATION: valine amide

<400> SEQUENCE: 20

Glu Val
1

<210> SEQ ID NO 21
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-tryptophan.

<400> SEQUENCE: 21

Glu Trp
1

<210> SEQ ID NO 22
<211> LENGTH: 2
<212> TYPE: PRT
<213> ORGANISM: Artificial Sequence
<220> FEATURE:
<223> OTHER INFORMATION: The peptide is a formed by condensation of the
      gamma-carboxy group of L-glutamic acid with the amino group of
      L-tyrosine.

<400> SEQUENCE: 22

Glu Tyr
1

<210> SEQ ID NO 23
<211> LENGTH: 2
<212> TYPE: PRT
<213> ORGANISM: Artificial Sequence
<220> FEATURE:
<223> OTHER INFORMATION: In the peptide, Val is
      Valinol(2-Amino-3-methyl-1-butanol)(Val-ol). The peptide is a
      formed by condensation of the gamma-carboxy group of L-glutamic
      acid with the amino group of Val-ol
<220> FEATURE:
<221> NAME/KEY: MISC_FEATURE
<222> LOCATION: (2)..(2)
<223> OTHER INFORMATION: valinol (2-amino-3-methyl-1-butanol)

<400> SEQUENCE: 23

Glu Val
```

-continued

```
<210> SEQ ID NO 24
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      glutamine. The carboxyl group of the glutamine residue is attached
      by normal peptide linkage to glutamic acid.

<400> SEQUENCE: 24

Glu Gln Glu
1

<210> SEQ ID NO 25
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      arginine. The carboxyl group of the arginie residue is attached by
      normal peptide linkage to glycine.

<400> SEQUENCE: 25

Glu Ala Gly
1

<210> SEQ ID NO 26
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      glutamic acid. The carboxyl group of the glutamic acid residue is
      attached by normal peptide linkage to glutamic acid.

<400> SEQUENCE: 26

Glu Glu Glu
1

<210> SEQ ID NO 27
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      isoleucine. The carboxyl group of the isoleucine residue is
      attached by normal peptide linkage to glycine.

<400> SEQUENCE: 27

Glu Ile Gly
1

<210> SEQ ID NO 28
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      proline. The carboxyl group of the proline residue is attached by
      normal peptide linkage to glycine.

<400> SEQUENCE: 28
```

Glu Pro Gly
1

<210> SEQ ID NO 29
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      glutamine. The carboxyl group of the glutamine residue is attached
      by normal peptide linkage to glutamine.

<400> SEQUENCE: 29

Glu Gln Gln
1

<210> SEQ ID NO 30
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      serine. The carboxyl group of the serine residue is attached by
      normal peptide linkage to glycine.

<400> SEQUENCE: 30

Glu Ser Gly
1

<210> SEQ ID NO 31
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain
      and threonine. The carboxyl group of the threonine residue is attached
      by normal peptide linkage to glycine.

<400> SEQUENCE: 31

Glu Thr Gly
1

<210> SEQ ID NO 32
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to glycine.

<400> SEQUENCE: 32

Glu Val Gly
1

<210> SEQ ID NO 33
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to alanine.

<400> SEQUENCE: 33

Glu Val Ala
1

<210> SEQ ID NO 34
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to cysteine.

<400> SEQUENCE: 34

Glu Val Cys
1

<210> SEQ ID NO 35
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to aspartic acid.

<400> SEQUENCE: 35

Glu Val Asp
1

<210> SEQ ID NO 36
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to glutamic acid.

<400> SEQUENCE: 36

Glu Val Glu
1

<210> SEQ ID NO 37
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to phenylalanine.

<400> SEQUENCE: 37

Glu Val Phe
1

<210> SEQ ID NO 38
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to histidine.

```
<400> SEQUENCE: 38

Glu Val His
1

<210> SEQ ID NO 39
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to lysine.

<400> SEQUENCE: 39

Glu Val Lys
1

<210> SEQ ID NO 40
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to methionine.

<400> SEQUENCE: 40

Glu Val Met
1

<210> SEQ ID NO 41
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to asparagine.

<400> SEQUENCE: 41

Glu Val Asn
1

<210> SEQ ID NO 42
<211> LENGTH: 3
<212> TYPE: PRT
<213> ORGANISM: Artificial Sequence
<220> FEATURE:
<223> OTHER INFORMATION: In the peptide, Xaa is ornithine(Orn). It is a
      tripeptide with a gamma peptide linkage between the carboxyl group
      of the glutamic acid side chain and valine. The carboxyl group of
      the valine residue is attached by normal peptide l
<220> FEATURE:
<221> NAME/KEY: MOD_RES
<222> LOCATION: (3)..(3)
<223> OTHER INFORMATION: Orn

<400> SEQUENCE: 42

Glu Val Xaa
1

<210> SEQ ID NO 43
<211> LENGTH: 3
<212> TYPE: PRT
<213> ORGANISM: Artificial Sequence
<220> FEATURE:
```

```
<223> OTHER INFORMATION: It is a tripeptide with a gamma peptide linkage
      between the carboxyl group of the glutamic acid side chain and
      valine. The carboxyl group of the valine residue is attached by
      normal peptide linkage to proline.

<400> SEQUENCE: 43

Glu Val Pro
1

<210> SEQ ID NO 44
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to arginine.

<400> SEQUENCE: 44

Glu Val Arg
1

<210> SEQ ID NO 45
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      valine. The carboxyl group of the valine residue is attached by
      normal peptide linkage to valine.

<400> SEQUENCE: 45

Glu Val Val
1

<210> SEQ ID NO 46
<211> LENGTH: 3
<212> TYPE: PRT
<213> ORGANISM: Artificial Sequence
<220> FEATURE:
<223> OTHER INFORMATION: In the peptide, Cys is Cys(s-Me), which is
      characterized in that the hydrogen of the thiol group is
      substituted with a methyl group. It is a tripeptide with a gamma
      peptide linkage between the carboxyl group of the glutamic acid
      side chain and Cys(s-Me).
<220> FEATURE:
<221> NAME/KEY: MISC_FEATURE
<222> LOCATION: (2)..(2)
<223> OTHER INFORMATION: cysteine in which hydrogen of the thiol group
      is substituted with a methyl group

<400> SEQUENCE: 46

Glu Cys Gly
1

<210> SEQ ID NO 47
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      Xaa. The carboxyl group of the Xaa residue is attached by normal
      peptide linkage to glycine. In the peptide, Xaa is 2-aminobutyric
      acid
<220> FEATURE:
<221> NAME/KEY: MOD_RES
<222> LOCATION: (2)..(2)
<223> OTHER INFORMATION: Abu
```

```
<400> SEQUENCE: 47

Glu Xaa Gly
1

<210> SEQ ID NO 48
<211> LENGTH: 3
<212> TYPE: PRT
<213> ORGANISM: Artificial Sequence
<220> FEATURE:
<223> OTHER INFORMATION: It is a tripeptide with a gamma peptide linkage
      between the carboxyl group of the glutamic acid side chain and
      leucine. The carboxyl group of the leucine residue is attached by
      normal peptide linkage to glycine.

<400> SEQUENCE: 48

Glu Leu Gly
1

<210> SEQ ID NO 49
<211> LENGTH: 2
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MOD_RES
<222> LOCATION: (2)..(2)
<223> OTHER INFORMATION: Abu

<400> SEQUENCE: 49

Glu Xaa
1

<210> SEQ ID NO 50
<211> LENGTH: 2
<212> TYPE: PRT
<213> ORGANISM: Artificial Sequence
<220> FEATURE:
<223> OTHER INFORMATION: peptide identified from yeast hydrolysate

<400> SEQUENCE: 50

Glu His
1

<210> SEQ ID NO 51
<211> LENGTH: 2
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MISC_FEATURE
<222> LOCATION: (1)..(1)
<223> OTHER INFORMATION: is beta-Glutamic acid

<400> SEQUENCE: 51

Xaa His
1

<210> SEQ ID NO 52
<211> LENGTH: 2
<212> TYPE: PRT
<213> ORGANISM: Artificial Sequence
<220> FEATURE:
<223> OTHER INFORMATION: peptide identified from yeast hydrolysate

<400> SEQUENCE: 52
```

Glu Lys
1

<210> SEQ ID NO 53
<211> LENGTH: 2
<212> TYPE: PRT
<213> ORGANISM: Artificial Sequence
<220> FEATURE:
<223> OTHER INFORMATION: peptide identified from yeast hydrolysate

<400> SEQUENCE: 53

Glu Met
1

<210> SEQ ID NO 54
<211> LENGTH: 2
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MOD_RES
<222> LOCATION: (2)..(2)
<223> OTHER INFORMATION: Nle

<400> SEQUENCE: 54

Glu Xaa
1

<210> SEQ ID NO 55
<211> LENGTH: 2
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MOD_RES
<222> LOCATION: (2)..(2)
<223> OTHER INFORMATION: Nva

<400> SEQUENCE: 55

Glu Xaa
1

<210> SEQ ID NO 56
<211> LENGTH: 2
<212> TYPE: PRT
<213> ORGANISM: Artificial Sequence
<220> FEATURE:
<223> OTHER INFORMATION: peptide identified from yeast hydrolysate

<400> SEQUENCE: 56

Glu Ser
1

<210> SEQ ID NO 57
<211> LENGTH: 2
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MISC_FEATURE
<222> LOCATION: (2)..(2)
<223> OTHER INFORMATION: is tert-Leucine

<400> SEQUENCE: 57

Glu Xaa
1

```
<210> SEQ ID NO 58
<211> LENGTH: 3
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MOD_RES
<222> LOCATION: (2)..(2)
<223> OTHER INFORMATION: Abu

<400> SEQUENCE: 58

Glu Xaa Leu
1

<210> SEQ ID NO 59
<211> LENGTH: 3
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MOD_RES
<222> LOCATION: (2)..(2)
<223> OTHER INFORMATION: Abu

<400> SEQUENCE: 59

Glu Xaa Pro
1

<210> SEQ ID NO 60
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 60

Glu Ala Phe
1

<210> SEQ ID NO 61
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 61

Glu Ala Ile
1

<210> SEQ ID NO 62
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 62

Glu Ala Leu
1

<210> SEQ ID NO 63
<211> LENGTH: 3
<212> TYPE: PRT
<213> ORGANISM: Artificial Sequence
```

```
<220> FEATURE:
<223> OTHER INFORMATION: peptide identified from yeast hydrolysate

<400> SEQUENCE: 63

Glu Ala Pro
1

<210> SEQ ID NO 64
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 64

Glu Ala Trp
1

<210> SEQ ID NO 65
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 65

Glu Ala Tyr
1

<210> SEQ ID NO 66
<211> LENGTH: 3
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MISC_FEATURE
<222> LOCATION: (3)..(3)
<223> OTHER INFORMATION: is beta-Alanine

<400> SEQUENCE: 66

Glu Cys Xaa
1

<210> SEQ ID NO 67
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 67

Glu Asp Phe
1

<210> SEQ ID NO 68
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 68

Glu Asp Met
1

<210> SEQ ID NO 69
```

```
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 69

Glu Glu Phe
1

<210> SEQ ID NO 70
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 70

Glu Glu Gln
1

<210> SEQ ID NO 71
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 71

Glu Phe Ala
1

<210> SEQ ID NO 72
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 72

Glu Phe Val
1

<210> SEQ ID NO 73
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 73

Glu Gly Ala
1

<210> SEQ ID NO 74
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 74

Glu Gly Gly
1

<210> SEQ ID NO 75
<211> LENGTH: 3
```

```
<212> TYPE: PRT
<213> ORGANISM: Artificial Sequence
<220> FEATURE:
<223> OTHER INFORMATION: peptide identified from yeast hydrolysate

<400> SEQUENCE: 75

Glu Gly Trp
1

<210> SEQ ID NO 76
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 76

Glu Gly Tyr
1

<210> SEQ ID NO 77
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 77

Glu Ile Ala
1

<210> SEQ ID NO 78
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 78

Glu Ile Phe
1

<210> SEQ ID NO 79
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 79

Glu Ile Ser
1

<210> SEQ ID NO 80
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 80

Glu Ile Thr
1

<210> SEQ ID NO 81
<211> LENGTH: 3
<212> TYPE: PRT
```

```
<213> ORGANISM: Artificial Sequence
<220> FEATURE:
<223> OTHER INFORMATION: peptide identified from yeast hydrolysate

<400> SEQUENCE: 81

Glu Ile Val
1

<210> SEQ ID NO 82
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 82

Glu Leu Asn
1

<210> SEQ ID NO 83
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 83

Glu Leu Ser
1

<210> SEQ ID NO 84
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 84

Glu Leu Val
1

<210> SEQ ID NO 85
<211> LENGTH: 3
<212> TYPE: PRT
<213> ORGANISM: Artificial Sequence
<220> FEATURE:
<223> OTHER INFORMATION: peptide identified from yeast hydrolysate
<220> FEATURE:
<221> NAME/KEY: MOD_RES
<222> LOCATION: (2)..(2)
<223> OTHER INFORMATION: Nva

<400> SEQUENCE: 85

Glu Xaa Gly
1

<210> SEQ ID NO 86
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 86

Glu Pro Asp
1
```

```
<210> SEQ ID NO 87
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 87

Glu Arg Tyr
1

<210> SEQ ID NO 88
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 88

Glu Ser Tyr
1

<210> SEQ ID NO 89
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 89

Glu Thr Cys
1

<210> SEQ ID NO 90
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 90

Glu Thr Asp
1

<210> SEQ ID NO 91
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 91

Glu Thr His
1

<210> SEQ ID NO 92
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 92

Glu Thr Gln
1

<210> SEQ ID NO 93
```

```
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 93

Glu Thr Arg
1

<210> SEQ ID NO 94
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 94

Glu Thr Ser
1

<210> SEQ ID NO 95
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 95

Glu Val Gln
1

<210> SEQ ID NO 96
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 96

Glu Val Ser
1

<210> SEQ ID NO 97
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 97

Glu Val Thr
1

<210> SEQ ID NO 98
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 98

Glu Trp Ala
1

<210> SEQ ID NO 99
<211> LENGTH: 3
```

```
<212> TYPE: PRT
<213> ORGANISM: Artificial Sequence
<220> FEATURE:
<223> OTHER INFORMATION: peptide identified from yeast hydrolysate

<400> SEQUENCE: 99

Glu Trp Cys
1

<210> SEQ ID NO 100
<211> LENGTH: 3
<212> TYPE: PRT
<213> ORGANISM: Artificial Sequence
<220> FEATURE:
<223> OTHER INFORMATION: peptide identified from yeast hydrolysate

<400> SEQUENCE: 100

Glu Trp Glu
1

<210> SEQ ID NO 101
<211> LENGTH: 18
<212> TYPE: DNA
<213> ORGANISM: Artificial Sequence
<220> FEATURE:
<223> OTHER INFORMATION: Nrf2 Forward primer

<400> SEQUENCE: 101
attccttcag cagcatcc                                                       18

<210> SEQ ID NO 102
<211> LENGTH: 18
<212> TYPE: DNA
<213> ORGANISM: Artificial Sequence
<220> FEATURE:
<223> OTHER INFORMATION: Nrf2 Reverse primer

<400> SEQUENCE: 102
gtgttgactg tggcatct                                                       18

<210> SEQ ID NO 103
<211> LENGTH: 19
<212> TYPE: DNA
<213> ORGANISM: Artificial Sequence
<220> FEATURE:
<223> OTHER INFORMATION: 18S Forward primer

<400> SEQUENCE: 103
gagcctgaga aacggctac                                                      19

<210> SEQ ID NO 104
<211> LENGTH: 19
<212> TYPE: DNA
<213> ORGANISM: Artificial Sequence
<220> FEATURE:
<223> OTHER INFORMATION: 18S Reverse primer

<400> SEQUENCE: 104
cccattattc ctagctgcg                                                      19

<210> SEQ ID NO 105
<211> LENGTH: 20
<212> TYPE: DNA
<213> ORGANISM: Artificial Sequence
<220> FEATURE:
<223> OTHER INFORMATION: SOD2 forward primer
```

```
<400> SEQUENCE: 105
gcacattaac gcgcagatca                                               20

<210> SEQ ID NO 106
<211> LENGTH: 20
<212> TYPE: DNA
<213> ORGANISM: Artificial Sequence
<220> FEATURE:
<223> OTHER INFORMATION: SOD2 reverse primer

<400> SEQUENCE: 106
agcctccagc aactctcctt                                               20

<210> SEQ ID NO 107
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 107
gtatgacaac agcctcaaga t                                             21

<210> SEQ ID NO 108
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 108
agtccttcca cgataccaaa                                               20
```

We claim:

1. A method for treating oxidative damage to cells in a subject in need thereof, wherein the method comprises orally administering to the subject at least one peptide selected from the group consisting of (i) the amino acid sequence γ-Glu-Xaa$^1$ or γ-Glu-Xaa$^2$-Xaa$^3$, and (ii) the amino acid sequence γ-Glu-Gln-Glu;

wherein

Xaa$^1$ is any one amino acid selected from histidine (H), glutamine (Q), or isoleucine (I);

Xaa$^2$ is any one amino acid selected from threonine (T) or valine (V), and wherein when Xaa$^2$ is threonine (T), Xaa$^3$ is glycine (G), wherein when Xaa$^2$ is valine (V), Xaa$^3$ is any one amino acid selected from cysteine (C), aspartic acid (D), glutamic acid (E), phenylalanine (F), methionine (M), asparagine (N), proline (P), glutamine (Q), and arginine (R); and wherein the subject is human or animal.

2. The method according to claim 1, wherein the oxidative damage to cells is caused by generation of free radicals or reactive oxygen species (ROS).

3. The method according to claim 1, wherein the at least one peptide is γ-Glu-Gln-Glu.

4. The method according to claim 1, wherein the at least one peptide is γ-Glu-His.

5. The method according to claim 1, wherein the at least one peptide is γ-Glu-Ile.

6. The method according to claim 1, wherein the at least one peptide is γ-Glu-Thr-Gly.

7. The method according to claim 1, wherein the at least one peptide is γ-Glu-Val-Cys.

* * * * *